US011491267B2

(12) United States Patent
Merchant et al.

(10) Patent No.: US 11,491,267 B2
(45) Date of Patent: Nov. 8, 2022

(54) METHOD FOR TAILORING DIALYSIS TREATMENT BASED ON SENSED POTASSIUM CONCENTRATION IN BLOOD SERUM OR DIALYSATE

(71) Applicant: Fresenius Medical Care Holdings, Inc., Waltham, MA (US)

(72) Inventors: Stephen Merchant, Oklahoma City, OK (US); Roland Levin, San Ramon, CA (US); Chris Chau, Mission, TX (US); Shakil Aslam, Lincoln, MA (US)

(73) Assignee: FRESENIUS MEDICAL CARE HOLDINGS, INC., Waltham, MA (US)

( * ) Notice: Subject to any disclaimer, the term of this patent is extended or adjusted under 35 U.S.C. 154(b) by 759 days.

(21) Appl. No.: 16/521,193

(22) Filed: Jul. 24, 2019

(65) Prior Publication Data
US 2020/0030515 A1 Jan. 30, 2020

Related U.S. Application Data

(60) Provisional application No. 62/711,163, filed on Jul. 27, 2018, provisional application No. 62/711,204, filed on Jul. 27, 2018.

(51) Int. Cl.
*A61M 1/16* (2006.01)
*A61M 1/34* (2006.01)
(Continued)

(52) U.S. Cl.
CPC ......... *A61M 1/1603* (2014.02); *A61B 5/0075* (2013.01); *A61B 5/02055* (2013.01);
(Continued)

(58) Field of Classification Search
CPC ............. A61M 1/1603; A61M 1/1609; A61M 1/1613; A61M 1/1635; A61M 1/1672;
(Continued)

(56) References Cited

U.S. PATENT DOCUMENTS 3,598,713 A 8/1971 Baum et al.
3,856,649 A 12/1974 Genshaw et al.
(Continued)

FOREIGN PATENT DOCUMENTS

EP 2701596 B1 9/2019

OTHER PUBLICATIONS

OPTI® CCA-TS2 Analyzer Operator's Manual; OPTI Medical Systems, Inc.; Roswell, GA, 325 pages (2016).
(Continued)

*Primary Examiner* — John Kim
(74) *Attorney, Agent, or Firm* — Kilyk & Bowersox, P.L.L.C.

(57) ABSTRACT

A method of dialysis is provided that includes sensing the concentration of potassium in a patient's blood serum, in used dialysate resulting from treating the patient, or in both. The method involves generating a sensed value of the concentration of potassium, comparing the sensed value with one or more values stored in a memory, and generating a control signal based on the comparison. Supplemental potassium solution is infused into the treatment dialysate, based on the control signal. The comparison can be made to patient-historical data, population data, or both.

18 Claims, 24 Drawing Sheets

(51) Int. Cl.

| | |
|---|---|
| A61M 1/36 | (2006.01) |
| G01N 27/333 | (2006.01) |
| G06F 3/14 | (2006.01) |
| G01Q 30/04 | (2010.01) |
| G01N 33/00 | (2006.01) |
| G01N 21/31 | (2006.01) |
| G01J 1/00 | (2006.01) |
| G01N 21/62 | (2006.01) |
| G01N 21/63 | (2006.01) |
| G01N 21/64 | (2006.01) |
| G01N 21/77 | (2006.01) |
| A61B 5/00 | (2006.01) |
| A61B 5/02 | (2006.01) |
| G01N 21/33 | (2006.01) |
| A61B 5/024 | (2006.01) |
| A61B 5/0205 | (2006.01) |

(52) U.S. Cl.
CPC ....... *A61B 5/02427* (2013.01); *A61M 1/1609* (2014.02); *A61M 1/1613* (2014.02); *A61M 1/1635* (2014.02); *A61M 1/1672* (2014.02); *A61M 1/1694* (2013.01); *A61M 1/1696* (2013.01); *A61M 1/342* (2013.01); *A61M 1/3424* (2014.02); *A61M 1/3455* (2013.01); *A61M 1/3607* (2014.02); *A61M 1/3609* (2014.02); *G01J 1/00* (2013.01); *G01N 21/31* (2013.01); *G01N 21/33* (2013.01); *G01N 21/62* (2013.01); *G01N 21/63* (2013.01); *G01N 21/631* (2013.01); *G01N 21/64* (2013.01); *G01N 21/6402* (2013.01); *G01N 21/7703* (2013.01); *G01N 27/333* (2013.01); *G01N 27/3335* (2013.01); *G01N 33/0067* (2013.01); *G01Q 30/04* (2013.01); *G06F 3/14* (2013.01); *A61M 2205/18* (2013.01); *A61M 2205/33* (2013.01); *A61M 2205/502* (2013.01); *A61M 2230/04* (2013.01); *A61M 2230/20* (2013.01)

(58) Field of Classification Search
CPC .. A61M 1/1694; A61M 1/1696; A61M 1/342; A61M 1/3424; A61M 1/3455; A61M 1/3607; A61M 1/3609; A61M 2205/18; A61M 2205/33; A61M 2205/502; A61M 2230/04; A61M 2230/20; A61B 5/0075; A61B 5/02427; A61B 5/02055; G01N 27/3335; G01N 33/0067; G01N 21/31; G01N 21/33; G01N 21/62; G01N 21/63; G01N 21/631; G01N 21/64; G01N 21/6402; G01N 21/7703; G01N 27/333; G01Q 30/04; G06F 3/14; G01J 1/00
See application file for complete search history.

(56) References Cited

U.S. PATENT DOCUMENTS

| | | |
|---|---|---|
| 4,276,141 A | 6/1981 | Hawkins |
| 4,340,457 A | 7/1982 | Kater |
| 4,361,473 A | 11/1982 | Young et al. |
| 4,461,998 A | 7/1984 | Kater |
| 4,535,786 A | 8/1985 | Kater |
| 4,753,888 A | 6/1988 | Chiang |
| 4,814,060 A | 3/1989 | Banks |
| 4,892,640 A | 1/1990 | Wolfbeis et al. |
| 4,902,399 A | 2/1990 | Durley, III et al. |
| 4,995,959 A | 2/1991 | Metzner |
| 5,964,994 A | 10/1999 | Craig et al. |
| 6,432,296 B1 | 8/2002 | Daniel et al. |
| 6,752,172 B2 | 6/2004 | Lauer |
| 7,097,630 B2 | 8/2006 | Gotch et al. |
| 7,368,231 B2 | 5/2008 | Yuan |
| 7,373,195 B2 | 5/2008 | Ye |
| 7,769,420 B2 | 8/2010 | Silver et al. |
| 7,790,112 B2 | 9/2010 | Vanaja et al. |
| 8,571,659 B2 | 10/2013 | Kane et al. |
| 8,765,060 B2 | 7/2014 | Buhlmann et al. |
| 8,802,152 B2 | 8/2014 | Keyser et al. |
| 9,132,217 B2 | 9/2015 | Soykan et al. |
| 9,144,640 B2 | 9/2015 | Pudil et al. |
| 9,297,797 B2 | 3/2016 | Situ et al. |
| 9,377,429 B2 | 6/2016 | Iwamoto |
| 9,399,090 B2 | 7/2016 | Collier et al. |
| 9,456,755 B2 | 10/2016 | Soykan et al. |
| 9,457,050 B2 | 10/2016 | Keyser et al. |
| 9,510,780 B2 | 12/2016 | Silver |
| 9,561,316 B2 | 2/2017 | Gerber et al. |
| 9,616,164 B2 | 4/2017 | Nuernberger |
| 9,707,328 B2 | 7/2017 | Pudil et al. |
| 9,731,061 B2 | 8/2017 | Kopperschmidt et al. |
| 9,814,412 B2 | 11/2017 | Zhang et al. |
| 9,855,379 B2 | 1/2018 | Pudil et al. |
| 9,861,658 B2 | 1/2018 | Keyser et al. |
| 9,878,086 B2 | 1/2018 | Kleinekofort |
| 2006/0025748 A1 | 2/2006 | Ye |
| 2007/0227886 A1 | 10/2007 | Vanaja et al. |
| 2008/0161665 A1 | 7/2008 | Ye |
| 2008/0264790 A1 | 10/2008 | Kamahori et al. |
| 2010/0252429 A1 | 10/2010 | Rao |
| 2012/0175253 A1 | 7/2012 | Kobayashi et al. |
| 2012/0175254 A1 | 7/2012 | Kobayashi et al. |
| 2012/0261260 A1 | 10/2012 | Li et al. |
| 2012/0277551 A1 | 11/2012 | Gerber et al. |
| 2012/0318739 A1 | 12/2012 | Kopperschmidt et al. |
| 2013/0168247 A1 | 7/2013 | Iwamoto |
| 2013/0168265 A1 | 7/2013 | Iwamoto |
| 2014/0174923 A1 | 6/2014 | Rao |
| 2015/0008122 A1 | 1/2015 | Thompson |
| 2016/0195491 A1 | 7/2016 | Rao |
| 2016/0271318 A1 | 9/2016 | Wiktor |
| 2016/0310655 A1 | 10/2016 | Wiktor et al. |
| 2017/0000936 A1 | 1/2017 | Soykan et al. |
| 2017/0304516 A1 | 10/2017 | Burnes et al. |

OTHER PUBLICATIONS

Corsi, Cristiana et al., "Noninvasive quantification of blood potassium concentration from ECG in hemodialysis patients," Scientific Reports, 7:42492, pp. 1-10 (Feb. 2017).

Mount, David B., "Clinical manifestations and treatment of hypokalemia in adults," UpToDate (Wolters Kluer); pp. 1-19 (Mar. 7, 2018).

Charytan, David M. et al., "Arrhythmia and Sudden Death in Hemodialysis Patients: Protocol and Baseline Characteristics of the Monitoring in Dialysis Study," Clinical Journal of the American Society of Nephrology, Apr. 7, 2016, 11(4):721-734.

Roberts Paul R. et al., "Monitoring of arrhythmia and sudden death in a hemodialysis population: The CRASH-ILR Study," PLOS ONE; pp. 1-15 (Dec. 14, 2017).

Kovesdy, Csaba P. et al., "Serum and Dialysate Potassium Concentrations and Survival in Hemodialysis Patients," American Society of Nephrology2, pp. 999-1007 (2007).

Sharma, Manoj K. et al., "On-line monitoring of electrolytes in hemodialysis: on the road towards individualizing treatment," Expert Review of Medical Devices, vol. 13, No. 10, pp. 933-943 (2016).

Palmer, Biff F., "Dialysate Composition in Hemodialysis and Peritoneal Dialysis," Chapter 2, (2000).

Agar, Baris U. et al., "Potassium kinetics during hemodialysis," Hemodialysis International, vol. 19, pp. 23-32 (2015).

Locatelli, Francesco et al., "Optimal composition of the dialysate, with emphasis on its influence on blood pressure," Nephrology Dialysis Transplantation, vol. 19, No. 4, pp. 785-796 (2004).

Abramova, Natalia et at., "Integrated multi-sensor chip with photocured polymer membranes containing copolymerised plasticizer for direct pH, potassium, sodium and chloride ions determination in blood serum," Talanta (Elsevier), vol. 79, issue 4 (Sep. 15, 2019), Abstract Only.

(56) References Cited

OTHER PUBLICATIONS

Sanders, Helen N., et al. "Effect of potassium concentration in dialysate on total body potassium," Journal of Renal Nutrition (Elsevier), vol. 8, issue 2 (Apr. 1998), Abstract Only.

Ipatov, Andrey et al. "Integrated multisenor chip with sequential injection technique as a base for 'electronic tongue' devices," Sensors and Actuators B: Chemical (Elsevier), vol. 131, Issue 1 (Apr. 14, 2008), Abstract Only.

Partial International Search Report (Form PCT/ISA/206 Annex) for International Patent Application No. PCT/US2019/043278, dated Oct. 8, 2019 (4 pages total).

Provisional Opinion Accompanying the Partial Search Report (EPO Form 1707) for International Patent Application No. PCT/US2019/043278, dated Oct. 8, 2019 (9 pages total).

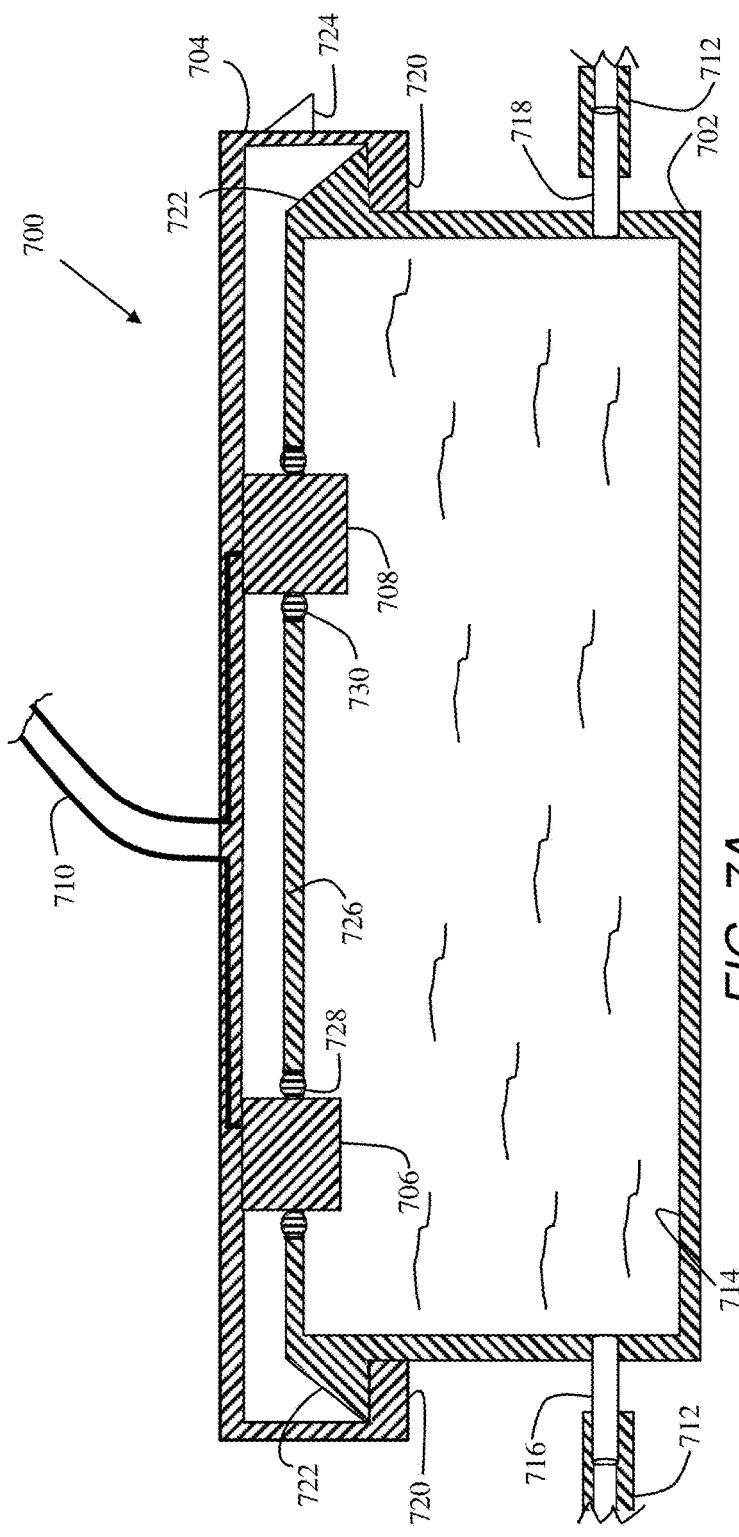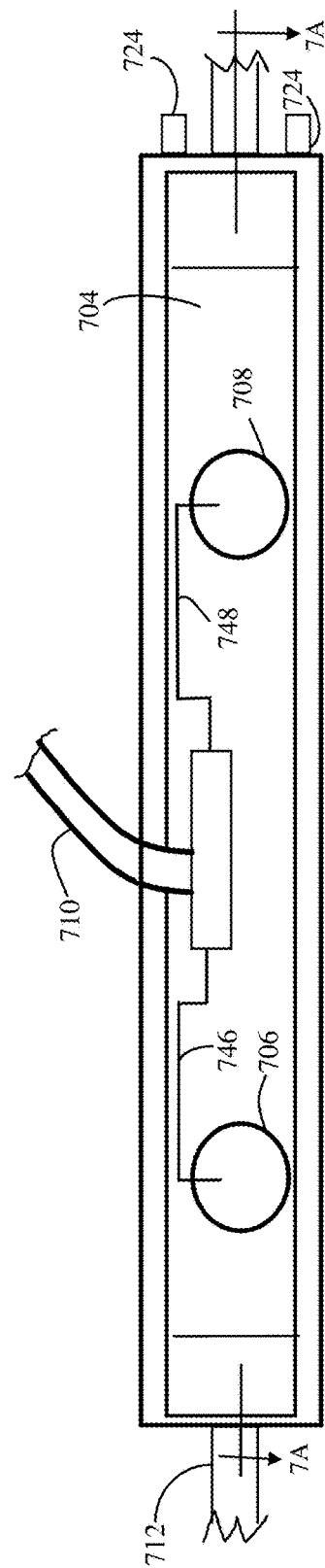
FIG. 7A
FIG. 7B

METHOD FOR TAILORING DIALYSIS TREATMENT BASED ON SENSED POTASSIUM CONCENTRATION IN BLOOD SERUM OR DIALYSATE

CROSS-REFERENCE TO RELATED APPLICATIONS

The present application claims priority to U.S. Provisional Patent Applications Nos. 62/711,163, and 62/711,204, both filed Jul. 27, 2018, and the benefit of U.S. patent application Ser. No. 16/521,159, filed Jul. 24, 2019, to Merchant et al., entitled "System for Tailoring Dialysis Treatment Based on Sensed Potassium Concentration, Patient Data, and Population Data," each of which is incorporated herein by reference in its entirety.

FIELD OF THE INVENTION

The present invention relates to blood treatment methods that involve regulating the concentration of potassium in a patient's bloodstream during the treatment.

BACKGROUND OF THE INVENTION

Dialysis treatments are typically administered intermittently and thus fail to provide continuous waste removal as enabled by a natural, functioning kidney. After a dialysis treatment, substances such as sodium and potassium salts begin to accumulate in the patient. Increasing the frequency and duration of dialysis treatments can help to more closely resemble continuous kidney function, but the need for patients to travel to a dialysis center, and the costs associated with each dialysis treatment, pose limits on the frequency with which patients can seek dialysis treatments.

As blood potassium concentration increases between dialysis treatments, patients become more susceptible to arrhythmias and at higher risk for developing hyperkalemia or sudden acute hypokalemia during hemodialysis. Hyperkalemia and hypokalemia increase the risk of cardiac arrhythmias. Generally, dialysis patients cannot effectively eliminate potassium from their bodies so potassium must be removed during dialysis treatments. Between treatments, however, blood potassium concentrations continually increase until the next treatment session. Cardiac arrhythmias including sudden cardiac death are among common causes of death in End-Stage Renal Disease (ESRD).

Removing potassium too quickly during a dialysis treatment can also lead to complications, including shock, atrial fibrillation, cardiac arrests, and arrhythmias. Dialysis patients often experience extreme variations in blood potassium concentrations during dialysis treatments, further increasing health risks. Thus, there is a need to guard against too sudden a change in blood potassium concentration during dialysis treatments. There is also a need to manage hyperkalemia, hypokalemia, and arrhythmias in dialysis patients, during and between treatment sessions.

SUMMARY OF THE PRESENT INVENTION

The present invention provides a dialysis method that comprises performing a dialysis treatment on a patient, sensing the concentration and/or amount of potassium in the patient's blood serum or spent dialysate during the treatment, generating a control signal based on the amount sensed, and modifying the dialysis treatment by infusing potassium solution into the treatment dialysis, based on the control signal. The potassium sensing device can be a potassium sensor configured to generate a sensed, measured, calculated, or computed potassium concentration value. A control and computing unit comprising a processor and a memory can control operation of the dialysis machine on which the treatment is carried out. The method can involve sending a sensed value signal to a control and computing unit that receives the signal from the potassium sensing device and processes the signal into the measured or calculated potassium concentration value. The processor can receive the sensed, measured, or calculated potassium concentration value, compare the value with one or more values stored in a memory, and generate a control signal based on the comparison.

According to the method, a potassium supply system can infuse potassium, for example, a potassium salt solution, into treatment dialysate that is used by the dialysis machine in treating the patient. The control and computing unit can be in data transfer communication with the potassium supply system, and the potassium supply system can be configured to receive the control signal and infuse the potassium solution into the treatment dialysate, based on the control signal. The control and computing unit can have a data processing unit, for example, a microprocessor, on which a data processing program, for example, software, can run.

The control and computing unit can store the measured or calculated value of potassium concentration in the memory, for example, to use it as historical data for future machine settings for the patient or to use it for other patients. The memory can have stored therein historical patient data pertaining to measured or calculated potassium concentration values of the same patient, obtained under the same and/or different patient parameters, or values of other patients. The different patient parameters that can be stored and used include at least one parameter based on the length of time since a last dialysis treatment has been carried out on the patient. An algorithm can be used that is based on inputted or looked-up data and the control signal can be based on the results of processing according to the algorithm.

Based on a patient's propensity to suffer from hyperkalemia, hypokalemia, or both, a kalemic constant can be assigned to the patient, for example, on a scale of from one to ten. The kalemic constant can be used to determine a line, curve, or slope defining the infusion rate of supplemental potassium for treating the patient over a treatment period.

The method can involve setting up a treatment based on patient-historical and/or population data. Records resulting from the treatment can be stored in a database of patient-historical and/or population data to provide more data points for, and to minimize deviations of, records in the database.

The method can involve sensing the concentration of potassium via any one of a number of different ways. Blood samples from the patient, or used dialysate resulting from treating the patient, can be invasively or non-invasively interrogated. The sensors can measure the concentration or send sensed value signals to a processor to be processed into a calculated or computed concentration value.

Additional features and advantages of the present invention will be set forth in part in the description that follows, and in part will be apparent from the description, or may be learned by practice of the present invention. The objectives and other advantages of the present invention will be realized and attained by means of the elements and combinations particularly pointed out in the description and appended claims.

BRIEF DESCRIPTION OF THE DRAWINGS

The present invention can be even more fully understood with the reference to the accompanying drawings which are intended to illustrate, not limit, the present invention.

FIG. 7A is a cross-sectional view of a flow cell for sensing blood potassium concentration in blood flowing through an extracorporeal blood circuit.

FIG. 7B is a top view of the flow cell show in FIG. 7A.

DETAILED DESCRIPTION OF THE PRESENT INVENTION

Figure 1A:
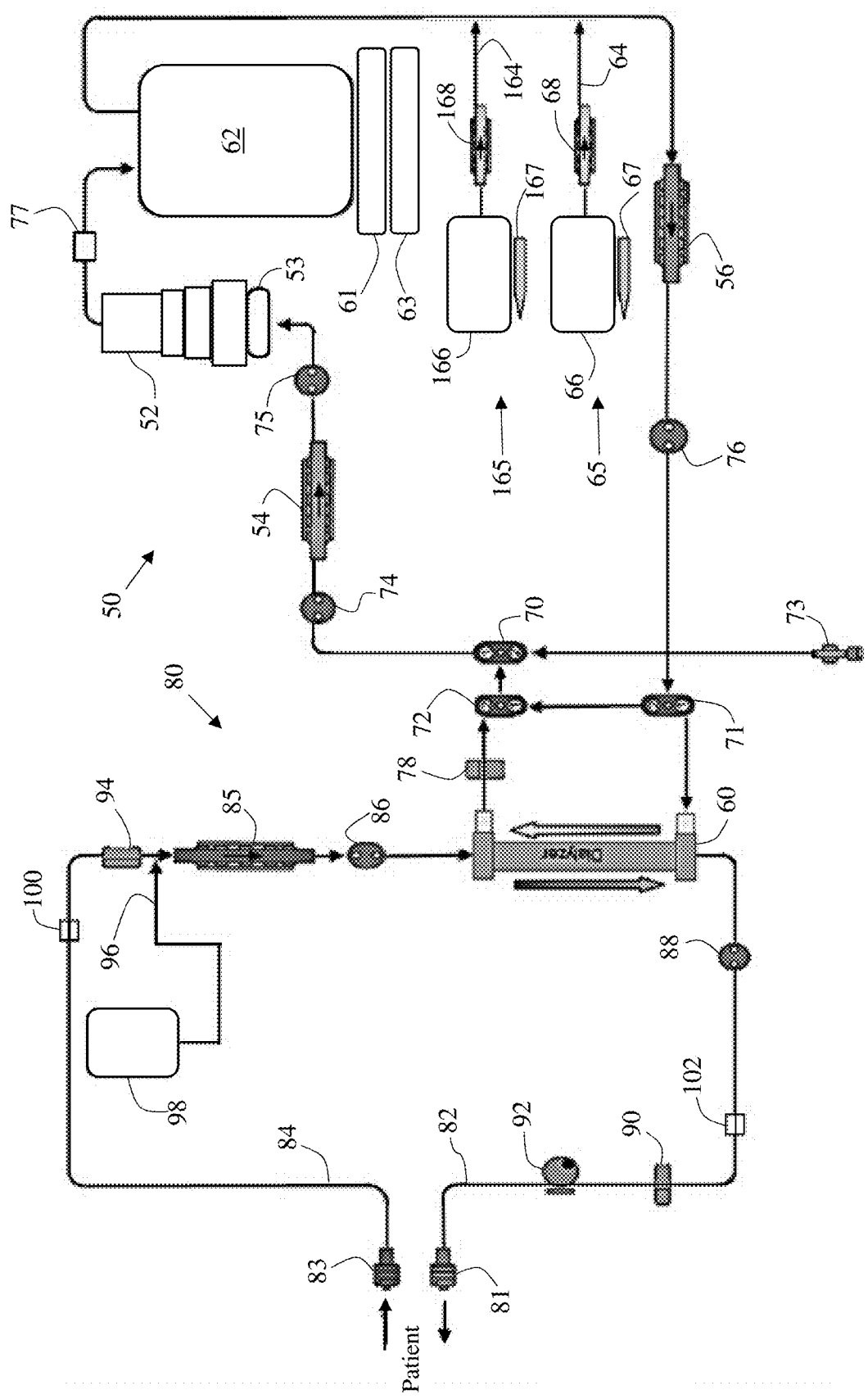
FIG. 1A is a schematic diagram of a dialysis system comprising an extracorporeal blood circuit, a regenerative dialysate circuit, and a potassium infusion circuit, in accordance with one or more embodiments of the present invention.

According to the present invention, a dialysis method is provided that comprises performing a dialysis treatment on a patient, sensing a concentration of potassium in the patient's blood serum or in used dialysate formed during the treatment, and modifying the dialysis treatment based on the sensed concentration. By sensing the concentration of potassium, a sensed value of potassium concentration can be generated by a potassium sensor. The sensed value can be sent, as a signal, to a control and computing unit that receives the sensed value signal, compares the sensed value signal with one or more values stored in a memory, and generates a control signal based on the comparison. The dialysis treatment can be modified by infusing a potassium solution into treatment dialysate used in the dialysis treatment, and the infusion can be controlled based on the control signal. In the case of sensing the concentration of potassium in the patient's blood serum, the sensed value can be a blood serum potassium concentration value. The sensed value can be saved in the memory or saved in a separate, different memory. The values stored in memory, with which the control and computing unit compares the sensed value, can include patient-historical data pertaining to sensed potassium concentration values of the same patient, but obtained under different patient parameters. The different patient parameters can include at least one parameter based on the length of time since a last dialysis treatment was carried out on the patient. Generating a control signal upon which the infusion of potassium solution can be based, can also comprise taking into account patient information inputted to the control and computing unit, including, for example, a time-since-last-treatment value.

Generating the control signal upon which the infusion of potassium can be based, can comprise comparing the sensed value of potassium concentration to potassium concentration values stored in a memory. The stored values can pertain to a population of different patients obtained under different patient parameters. The method can generate a control signal based on the sensed value of potassium concentration and based on population data stored in the memory. For example, a sensed value of blood serum potassium concentration can be compared to blood serum potassium concentration values of a population of different patients obtained under different patient parameters, such as population data stored in the memory.

The dialysis treatment performed on the patient can be performed using a single-pass dialysis machine or a sorbent-based, multi-pass dialysis machine that regenerates used dialysate with a sorbent cartridge. The dialysis method can comprise a hemodialysis treatment, a hemodiafiltration treatment, an acute hemodialysis treatment, a peritoneal dialysis treatment, an ultrafiltration dialysis treatment, or the like.

Sensing the concentration of potassium can comprise any of a number of different potassium sensing methods and can use any of a number of different potassium sensors. An ion selective electrode pair can be used to generate ion selective electrode measurements, and the method can comprise calculating the concentration of potassium based on the ion selective electrode measurements. The sensing can comprise directing ultraviolet light through the patient's blood and sensing the transmission of the ultraviolet light through the blood, or the absorption of ultraviolet light by the blood. The sensing can comprise directing near-infrared radiation through the patient's blood and sensing the transmission of near-infrared radiation through the blood or sensing the absorption of near-infrared radiation by the blood.

Sensing the concentration of potassium can comprise subjecting a portion of the patient's blood to flame photometry and sensing emissions resulting from the flame photometry. A portion of the patient's blood can be subjected to fluorescent excitation radiation and sensing the concentration of potassium can comprise sensing fluorescent photoinduced electron transfer resulting from exposure to the radiation. A portion of the patient's blood can be subjected to laser-induced breakdown spectroscopy and sensing the concentration of the potassium can comprise sensing spectroscopic emissions resulting from radiation with the laser beam.

Other methods of sensing the concentration of potassium, that can be used, include processing a portion of the patient's blood with a microfluidic chip. A portion of the patient's blood can be flowed through a microfluidic channel on a microfluidic chip where it is exposed to electromagnetic radiation directed through an optical fiber, toward the blood in the microfluidic channel. The source of electromagnetic radiation can be selected such that it causes fluorescent emissions to be emitted from components of the blood in the microfluidic channel. The fluorescent emissions can be collected and transmitted by through a second optical fiber toward a fluorescent detector. The fluorescence can be detected by the fluorescent detector and can be used by the detector alone, or with a separate processor, to generate concentration values of the various components, including at least potassium, in the blood.

Non-invasive methods can be used to compute the concentration of potassium in a patient's blood, for example, based on electrocardiogram signals. Electrocardiogram signals corresponding to a heartbeat of the patient can be sensed by an electrocardiogram lead connected to the patient. The amplitude of the T wave component of a heartbeat signal can be determined, for example, measured, along with a negative slope of the T wave component. A ratio of the negative slope to the amplitude can be computed and the ratio can then be correlated to a predetermined blood serum potassium concentration value stored in a memory. The ratio can be an average ratio that has been averaged from multiple heartbeat signals of the patient, for example, over a period of time such as 15 seconds or 60 seconds. Other non-invasive potassium concentration sensing techniques can be used that entail scaling multiple electrocardiogram signal components, summing the scaled values, and correlating the sum with a potassium concentration value stored in a memory, logged in a look-up table, or otherwise made available.

Many of the same potassium concentration sensing methods used to determine a blood serum potassium concentration can also be used to determine a potassium concentration in used dialysate. The method can include estimating blood serum potassium concentration based on a sensed value of potassium concentration in the used dialysate. Sensed values of potassium concentration in used dialysate can be compared to sensed values stored in a memory, to generate a control signal. A dialysis treatment can be modified by infusing potassium solution into fresh treatment dialysate to be used during the dialysis treatment, based on the control signal. The invasive and non-invasive methods of sensing blood serum potassium concentration, described herein, can similarly be used to sense and determine potassium concentration values in used dialysate. In an exemplary peritoneal dialysis method, used dialysate in the form of used peritoneal dialysis solution that has dwelled in a patient's peritoneum, can be subjected to potassium concentration sensing so that the patient's blood serum potassium concentration from the computed, calculated, or accurately estimated from the potassium concentration value of the used dialysate.

FIG. 1A is a flow path diagram for a hemodialysis machine comprising a dialysate circuit 50 and an extracorporeal blood circuit 80. Dialysate circuit 50 includes a sorbent cartridge 52 for regenerating used dialysate. A first dialysate pump 54 and a second dialysate pump 56 circulate dialysate through dialysate circuit 50 including through the dialysate-side of a dialyzer 60. The pump can move the dialysate through sorbent cartridge 52, into a dialysate reservoir 62, out of dialysate reservoir 62, and back through dialyzer 60. Downstream of dialysate reservoir 62, but upstream of second dialysate pump 56, and electrolytes infusion line 64 merges with the dialysate circuit so that electrolytes, for example, that may have been removed from the dialysate, by sorbent cartridge 52, can be replenished or replaced and thus available for transfer, through dialyzer 60, into extracorporeal blood circuit 80. Electrolytes infusion line 64 is part of an electrolytes circuit 65 that also includes an electrolytes container 66, a container level sensor 67, and an electrolytes pump 68. Electrolytes pump 68 is configured to move a concentrated electrolytes solution from electrolytes container 66 through electrolytes infusion line 64 and into the dialysate tubing of dialysate circuit 50, between dialysate reservoir 62 and second dialysate pump 56.

A potassium infusion circuit 165 separately provides for the controlled infusion of potassium into the dialysate tubing of dialysate circuit 50. A potassium infusion line 164 merges with dialysate circuit 50 downstream of sorbent cartridge 52 and downstream of dialysate reservoir 62, but upstream of second dialysate pump 56 and upstream of dialyzer 60. Potassium infusion circuit 165 comprises a potassium solution container 166 and a potassium infusate pump 168 configured to move a concentrated potassium infusate solution from potassium solution container 166 and through potassium infusion line 164. The level of potassium infusate solution can be monitored via a level detector 167 and the amount and rate of potassium infused can thus be measured, calculated, or both.

Dialysate circuit 50 is also provided with a fill and drain valve 70, a bypass IN valve 71, and a bypass OUT valve 72. The valves enable filling of dialysate circuit 50 with dialysate from a jug or other source, through a fill and drain port 73, and draining of dialysate circuit 50 through fill and drain port 73. When fill and drain valve 70 is closed, dialysate can neither be filled into nor drained from dialysate circuit 50.

With dialysate fill and drain valve 70 in a closed position, bypass IN valve 71 and bypass OUT valve 72 can be operated to enable circulation of dialysate through dialysate circuit 50 with or without bypassing flow through dialyzer 60. Bypassing can be useful, for example, for priming, filling, and draining dialysate circuit 50. Pressure sensors 74, 75, and 76 are used to monitor the pressure in dialysate circuit 50 and can be used to control the pump speed of one or both of first dialysate pump 54 and second dialysate pump 56. Dialysate circuit 50 also comprises an ammonium sensor 77 adjacent to, and downstream from, sorbent cartridge 52 and upstream of dialysate reservoir 62.

Dialysate reservoir 62 can rest on or be suspended from a scale 61 and, through scale 61, or independent of scale 61, can be in thermal contact with a heater and thermistor unit 63 that comprises a heater and a thermistor, thermometer, or other temperature sensing device. A scale 53 can also be provided for weighing sorbent cartridge 52. Based on the combined weight detected by reservoir scale 61 and sorbent cartridge scale 52 and based on known volumes of the tubing and dialyzer of dialysate circuit 50, the volume, weight, or other amount of dialysate in dialysate circuit 50 can be determined, monitored, and controlled so as to pull fluid off of a patient, infuse a certain amount of dialysate into a patient, or maintain a certain patient weight.

Dialysate circuit 50 can also comprise, or pass-through, a blood leak sensor 78 adjacent to and immediately downstream of dialyzer 60, to sense the presence of blood in the dialysate. Blood leak sensor 78 can comprise, for example, an optical blood leak sensor.

Extracorporeal blood circuit 80 comprises a to-patient connector 81 at the end of a venous return line 82, a from-patient connector 83 at an end of an arterial line 84, and the blood-side of dialyzer 60. A blood pump 85 is configured to pull blood from a patient through arterial line 84 and push the blood through dialyzer 60 and back to the patient through venous return line 82. A blood flow IN pressure sensor 86 is provided along blood circuit 80 downstream of blood pump 85 but upstream of dialyzer 60. A blood flow OUT pressure sensor 88 is proved along blood circuit 80 downstream of dialyzer 60, along venous return line 82. An air bubble sensor 90 and a pinch valve 92 are also provided along venous return line 82. Control electronics are provided such that, in the event that air bubble sensor 90 senses air in venous return line 82, a control signal is sent to pinch valve 92 to pinch-shut venous return line 82 and prevent the air from entering the patient's bloodstream.

Along arterial line 84 are provided an occlusion detector 94, and a connection to a saline supply line 96. For the connection, a T-connector, Y-connector, two-way valve, or the like, can be used. A saline bag 98 supplies saline, and optionally anticoagulant, to saline supply line 96. A medicine part (not shown) can be provided along saline supply line 96.

In accordance with the present teachings, extracorporeal blood circuit 80 can comprise a first potassium sensor 100 along arterial line 84 upstream of the connection to saline supply line 96, and a second potassium sensor 102 along venous return line 82. While two sensors are shown and described, it is to be understood that it is possible to use only one of the first and second potassium sensors, or both. The use of just a single potassium sensor, along either arterial line 84 or venous return line 82, can be implemented and is still within the spirit and scope of the present teachings. Control signals generated by one or both of first and second potassium sensors 100 and 102 can be sent over wired or wireless communication lines and used by a processor to control the operation and speed of potassium pump 168 so that the concentration of potassium in the dialysate can be carefully controlled. The careful control can provide a slow and gradual reduction in potassium blood level concentration such that the patient will neither be subject to nor feel the effects of sudden drastic changes in potassium concentrations during treatment.

Figure 1B:
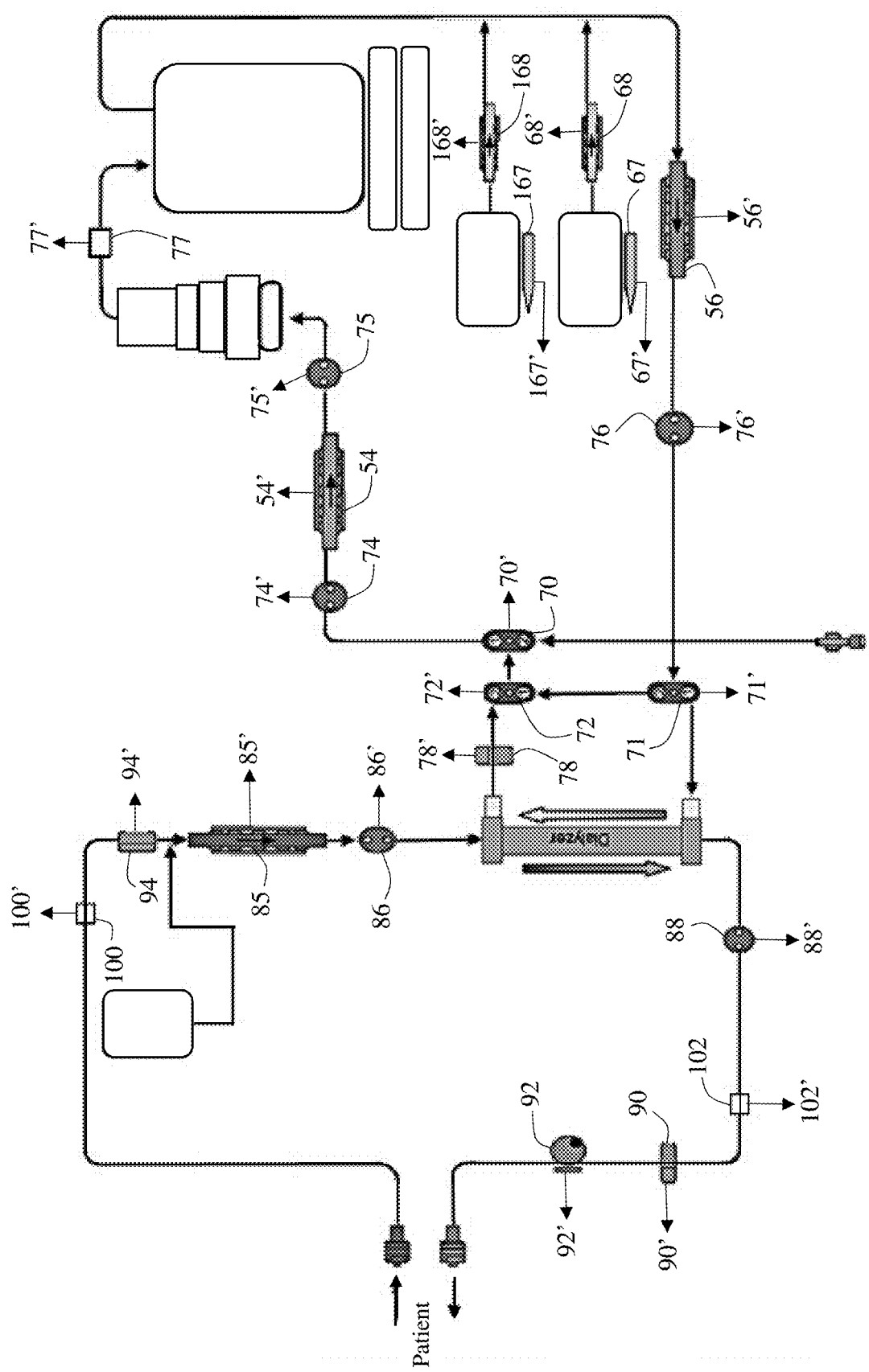
FIGS. 1B and 1C are schematic diagrams of the electronic circuitry of the dialysis system shown in FIG. 1A.
Figure 1C:
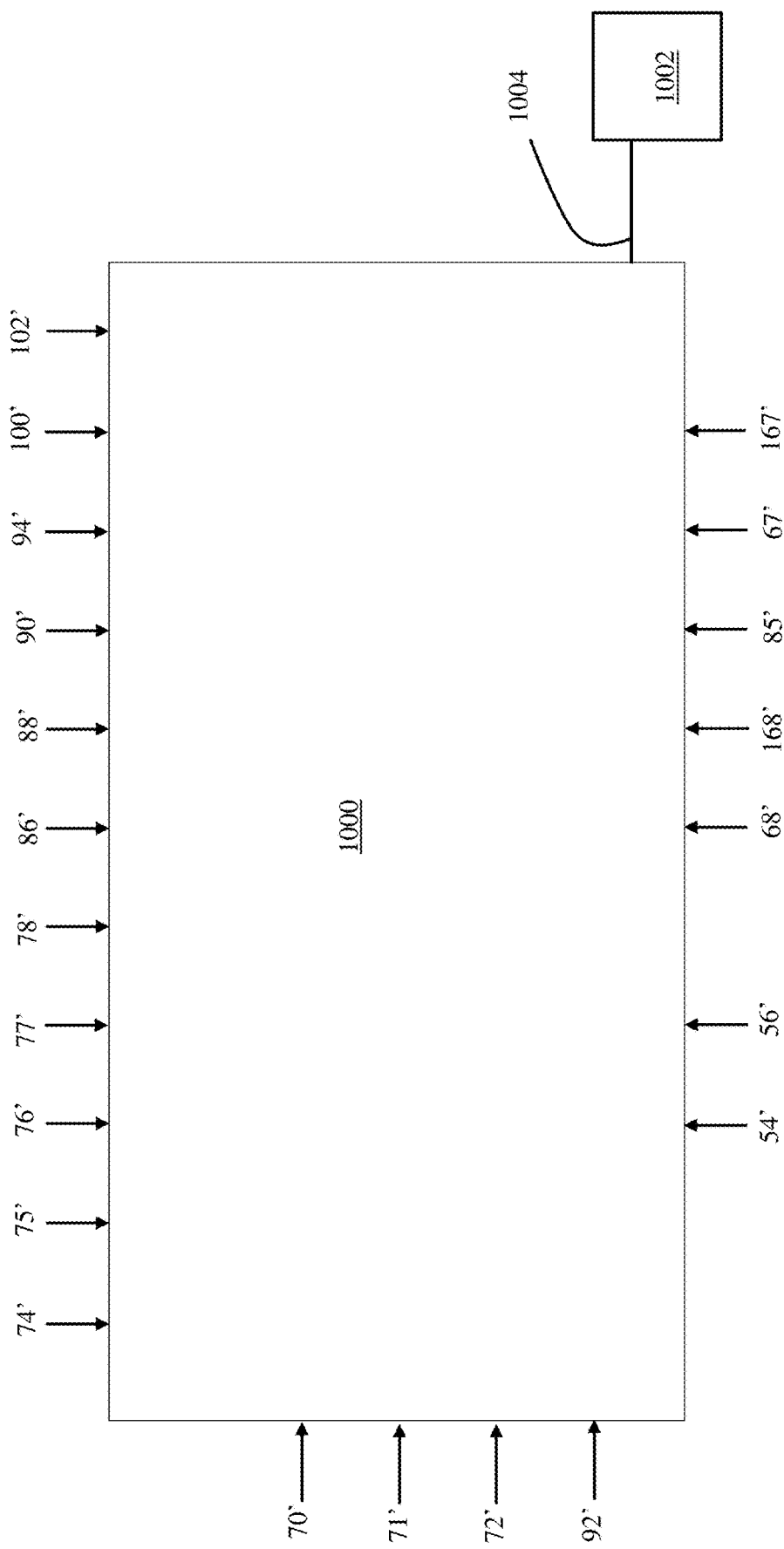

As shown in FIG. 1B, each of the pumps, valves, sensors, and detectors shown corresponds to the respective pumps, valves, sensors, and detectors described in connection with FIG. 1A, and identical reference numbers refer to identical components. As can be seen in FIG. 1B, each of the pumps, valves, sensors, and detectors is provided with a control line for sending signals to and/or receiving control signals from a control unit 1000 as shown in FIG. 1C. The control unit can have a data processing unit, for example, a processor or microprocessor, on which a data processing program, for example, software, can run. Each of the control lines has been designated using the same reference numeral as the component to which it is connected, but with an added apostrophe or prime (') notation so as to be distinguished from its corresponding component. While the various control lines are shown with arrow heads leading away from the corresponding components in FIG. 1B, and towards control unit 1000 in FIG. 1C, it is to be understand that the control lines can be for sending and/or receiving signals to and/or from control unit 1000. Each of the control lines can independently comprise a wire, cable, coaxial cable, harness, trace, or other electrically conductive lead, but it is also to be understood that signals can be sent to and from the various components and to and from control unit 1000 wirelessly, for example, using Wi-Fi or Bluetooth technologies, or the like.

A memory 1002 can be a part of or independent from control unit 1000 and can be in data transfer communication, with control unit 1000 or components thereof. As shown in FIG. 1C, a data transfer line 1004 connects control unit 1000 to memory 1002 so that data can be sent from control unit 1000 to be stored in memory 1002 and data can be retrieved from memory 1002 to be used by control unit 1000. Memory 1002 can comprise a read-write memory such that data acquired by control unit 1000 via the various sensors and detectors can be stored in memory 1002 and can be used during a current or future treatment session or to provide data to a patient historical database, a patient population database, or the like.

Control unit 1000 can comprise a processor, microprocessor, central processing unit (CPU), computer, or other processing device. Control unit 1000 can comprise multiple processors, a comparator, a regulator, logic circuitry, and the like components as would be recognized by those of skill in the art. Control unit 1000 can be a component of a central control unit of the treatment device. The central control unit can have a data processing unit, for example, a microprocessor, on which a data processing program, for example, software, can run.

As shown in FIGS. 1B and 1C, pumps 54, 56, 68, 85, and 168 are connected by means of control lines 54', 56', 68', 85', and 168', respectively, to control unit 1000. Valves 70, 71, and 72 are configured to receive control signals from control unit 1000 via control lines 70', 71', and 72', respectively. Pinch-valve 92 is configured to receive control signals from control unit 1000 via control line 92'. Control unit 1000 is configured to receive pressure signals from pressure sensors 74, 75, 76, 86, and 88, via control lines 74', 75', 76', 86', and 88', respectively. Control of the various pumps and valves can be based on pressure signals received from the pressure sensors as well as based on sensed and detected conditions, acquired by the other various sensors and detectors, which are sent to control unit 1000 over respective control lines. Potassium concentration sensors 100 and 102 are configured to send potassium concentration signals to control unit 1000 via control lines 100' and 102', respectively. An air bubble sensor signal can be sent to control unit 1000 from air bubble sensor 90 via control line 90'. A blood leak sensor signal can be sent from blood leak sensor 78 to control unit 1000 via control line 78'. An occlusion detector signal can be sent from occlusion detector 94 to control unit 1000 via control line 94'. An ammonia sensor signal can be sent from ammonia sensor 77 to control unit 1000 via control line 77'.

The level of concentrated electrolytes solution in electrolytes container 66 can be sensed by level sensor 67 and a signal corresponding to the sensed level can be sent to control unit 1000 via control line 67'. The level of concentrated potassium infusate solution in container 166 can be sensed by level sensor 167 and a signal corresponding to the sensed level can be sent from level sensor 167 to control unit 1000 via control line 167'.

Control unit 1000 can be configured to take into account the potassium concentrations sensed by potassium sensor 100, potassium sensor 102, or both, in determining whether, and how much, supplemental potassium should be pumped into the dialysate circuit via potassium infusion circuit 165. Control unit 1000 is configured, in response to the signals received, to send a control signal to the potassium infusate pump 168 via control line 168' to control infusion of supplemental potassium so as to achieve a prescribed potassium concentration in the dialysate, the blood, or both. The level of concentrated potassium infusate solution sensed by level sensor 167 can be sent as a signal via control line 167' to control unit 1000 so that the amount of supplemental potassium infused can be carefully controlled and regulated. Although FIGS. 1A-1C depict two potassium concentration sensors along blood circuit 80, it is to be understand that potassium concentration sensors can additionally, or instead, be provided along dialysate circuit 50 and the control of potassium concentration in a dialysate can be used to control, predict, estimate, and/or extrapolate the concentration of potassium in a patient's blood.

For detecting the concentration of potassium in a patient's blood, one or more potassium concentration sensors can be implemented in the extracorporeal blood circuit. Many devices and systems are known to those skilled in the art and can be implemented in accordance with the present teachings. Chemical sensors that have heretofore been implanted in a patient can be incorporated into an extracorporeal blood circuit as if the circuit were a part of the human anatomy. In this regard, the extracorporeal blood circuit can include a flow cell wherein an otherwise implantable medical device can be mounted or contacted in a configuration that enables sensing of potassium in blood flowing through the flow cell in the extracorporeal blood circuit. An exemplary implantable medical device for such a purpose can, for example, be a device as described in U.S. Pat. No. 8,571,659 B2 to Kane et al., which is incorporated herein in its entirety by reference. Another sensor that can be implemented and incorporated into an extracorporeal blood circuit is one or more of the devices described in U.S. Pat. No. 9,510,780 B2 to Silver, which is incorporated herein in its entirety by reference. Any of a wide variety of ion selective electrodes can also be used, for example, mounted in or on a flow cell included as a component of the extracorporeal blood circuit. The flow cell can be configured as a disposable component and the ion selective electrode or other potassium sensor device can be plugged into the flow cell, disconnected after use, and sterilized for reuse. In other words, the potassium sensor need not be a disposable component but can, if desired, be configured as a part of the extracorporeal blood circuit disposable tubing system.

Exemplary potassium sensors comprising ion selective electrodes include those described in U.S. Pat. No. 9,377,429 B2 to Iwamoto, U.S. Pat. No. 9,297,797 B2 to Situ et al., U.S. Pat. No. 8,765,060 B2 to Buhlmann et al., U.S. Pat. No. 7,790,112 B2 to Vanaja et al., U.S. Pat. No. 7,373,195 B2 to Ye, U.S. Pat. No. 7,368,231 B2 to Yuan, U.S. Pat. No. 6,432,296 B1 to Daniel et al., U.S. Pat. No. 5,964,994 to Craig et al., U.S. Pat. No. 4,902,399 to Durley, III et al., U.S. Pat. No. 4,892,640 to Wolfbeis et al., U.S. Pat. No. 4,814,060 to Banks, U.S. Pat. No. 4,535,786 to Kater, U.S. Pat. No. 4,461,998 to Kater, U.S. Pat. No. 4,361,473 to Young et al., U.S. Pat. No. 4,340,457 to Kater, U.S. Pat. No. 4,276,141 to Hawkins, U.S. Pat. No. 3,856,649 to Genshaw et al., and 3,598,713 to Baum et al. Other exemplary potassium sensors comprising ion selective electrodes include those described in U.S. Patent Application Publications Nos. US 2016/0195491 A1 to Rao, US 2015/0008122 A1 to Thompson, US 2014/0174923 A1 to Rao, US 2013/0168247 A1 to Iwamoto, US 2012/0261260 A1 to Li et al., US 2012/0175254 A1 to Kobayashi et al., US 2012/0175253 A1 to Kobayashi et al., US 2010/0252429 A1 to Rao, and US 2008/0264790 A1 to Kamahori et al. Each of the patents and published applications mentioned herein is incorporated by reference herein, in its entirety.

Signals corresponding to sensed potassium concentrations can be sent to a control unit to be used in an algorithm designed to provide a target prescription for the infusion of supplemental potassium into a dialysate circuit used for dialyzing blood in the extracorporeal blood circuit. The control unit can have a data processing unit, for example, a processor or microprocessor, on which a data processing program, for example, software, can run.

In an exemplary method using an exemplary system, a goal can be set to reduce potassium concentration in a patient, within a certain, prescribed, or otherwise set, time of treatment. The goal can be a reduction in potassium concentration such that the concentration ends up being within a certain range or ends up crossing a certain threshold. Range and threshold values can be inputted according to a prescription. The range or threshold can be from 1.5 mEq/L to 4.0 mEq/L, from 1.75 mEq/L to 3.5 mEq/L, from 2.0 mEq/L to 3.25 mEq/L, or from 2.0 mEq/L to 2.5 mEq/L. An endpoint concentration can be set using an input pad, screen, or keyboard, or can be automatically set from a downloaded or otherwise input prescription. Once the target or inputted concentration is attained, as measured by one or more potassium sensors, the delivery of any supplemental potassium via a potassium infusion circuit can be ceased.

To achieve such a reduction in potassium concentration most safely for a patient, a gradual reduction in potassium concentration, over the majority of a treatment session, can be achieved by infusing a concentrated, supplemental supply of potassium to a dialysate circuit. The concentrated, supplemental supply of potassium can be infused upstream of a dialyzer in a single-pass hemodialysis system. The concentrated, supplemental supply of potassium can be infused upstream of a dialyzer and downstream of a sorbent or regenerative cartridge in a multi-pass hemodialysis system. Instead, or in addition, a supplemental supply of potassium can be added to a substituate or replacement fluid, to enable pre-dilution, post-dilution, or both, in a hemodiafiltration system. By "supplemental potassium" what is meant is that the potassium is supplemental to any potassium that is otherwise already added to a dialysate or replacement fluid from an electrolyte or infusate mix that might also contain sodium, calcium, magnesium, bicarbonate, and the like, well-known components used in the preparation, replenishment, and maintenance of dialysate. Such an electrolytes mix can be infused by an electrolytes infusion circuit as described herein.

Figure 2A:
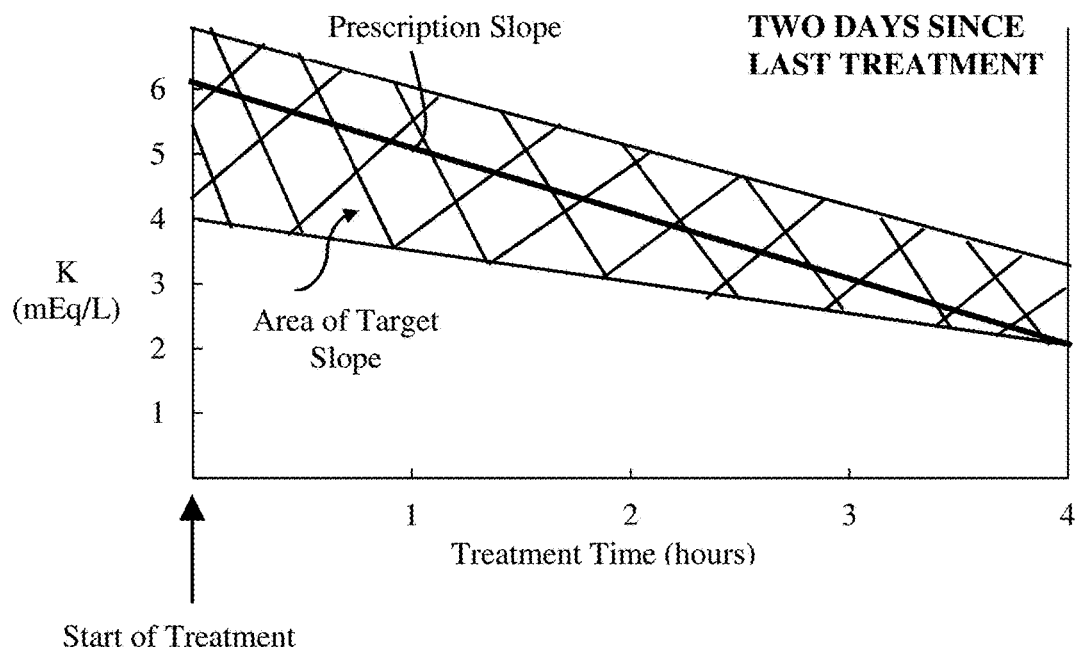
FIG. 2A is a graph showing a target slope area and a prescribed slope for the gradual reduction of blood potassium concentration in a patient's blood over the course of a dialysis treatment.

FIG. 2A is a graph showing an area of target slope for reducing the concentration of potassium in a patient over the course of a blood treatment. A prescription, for example, based on an algorithm as described herein, can be downloaded or otherwise inputted into a central processor of a blood treatment system. Using signals received from potassium concentration sensors, the central processor can send control signals to a potassium infusion circuit so that a supplemental supply of concentrated potassium can be infused into a dialysate or replacement fluid used by the blood treatment system. Infusion can be controlled such that the amount of potassium to be infused can be calculated to enable a gradual decrease in potassium concentration over a good part of or an entire treatment session, for example, over the entire four-hour treatment session exemplified in FIGS. 2A and 2B.

Figure 2B:
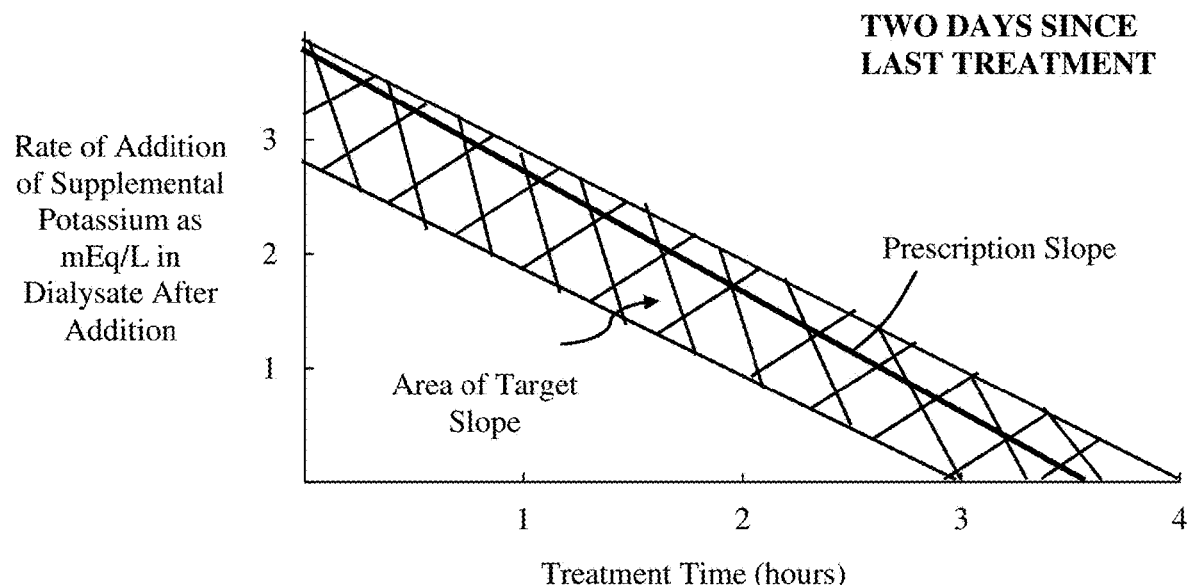
FIG. 2B is a graph showing a target slope area and a prescribed slope for the gradual reduction of the infusion of supplemental potassium over the course of a treatment, to achieve the reduction in blood potassium concentration prescribed in FIG. 2A.

In FIG. 2B, a graph is shown depicting the rate of supplemental potassium infusion over the same four-hour treatment period shown in FIG. 2A. To achieve the goal or target slope illustrated in FIG. 2A, that is based on an inputted prescription including the target slope shown in FIG. 2A, a gradual reduction in a rate of supplemental potassium infusion, as shown in FIG. 2B, can be enabled by the system. Potassium sensing before and after treatments can be used by the algorithm, for example, as data points, to further and better define target zones of slope, target rates of change, and target reductions of infusion rates, and to build a multi-dimensional database of results. Such a multi-dimensional database can be useful to define an optimum treatment prescription for a particular patient under a particular set of conditions.

Each of the prescription slopes shown in FIGS. 2A and 2B can be prescribed by a physician based on any number of factors, different conditions, historical data of the patient, population data, or the like. One exemplary method that a physician can use to prescribe a slope for the gradual reduction of supplemental potassium infusion involves applying knowledge of the patient's propensity or likelihood to be affected by hypokalemia, deduced from analysis of historical dialysis treatments on the patient. While evaluating the effects of hypokalemia can be subjective, a physician or clinician can evaluate physiological properties and/or conditions of the patient after each of a plurality of dialysis treatments. The patient's input such as answers to questions and replies to inquiries can be useful in evaluating the patient and the effects of the treatment. Blood pressure, heart beat rate, and potassium blood test results can be evaluated. The evaluator can then scale the patient's propensity to be affected by hypokalemia, based on the evaluation. The patient's propensity to suffer or to be affected can, for example, be scaled on a scale of from 0 (zero) to 10 (ten).

Figure 2C:
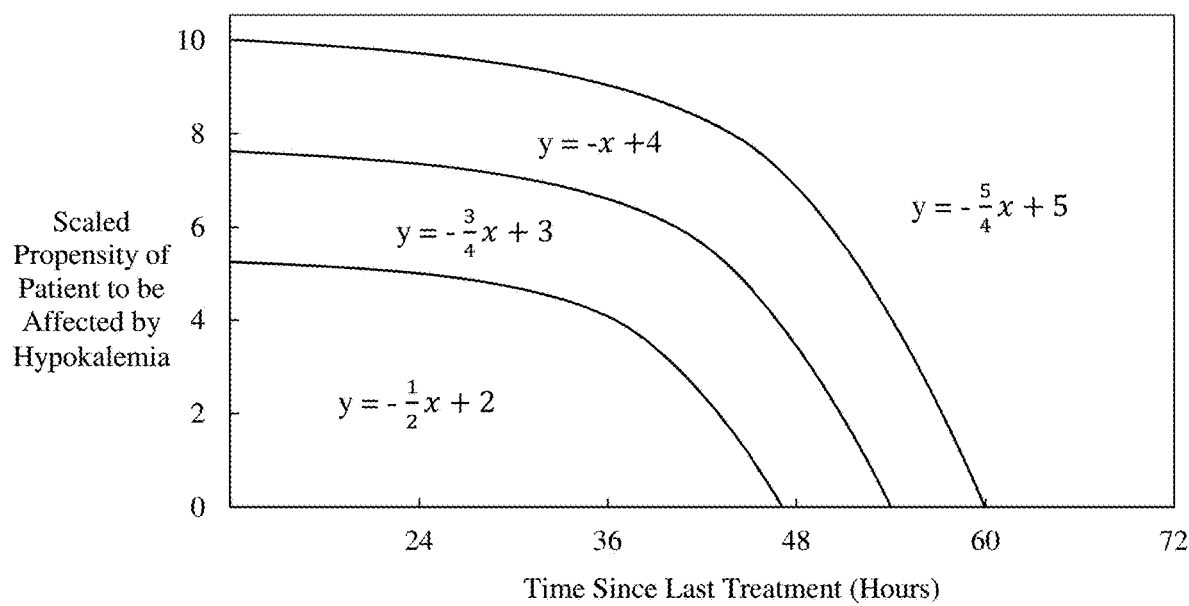
FIG. 2C is a graph showing the slope of reduction of the infusion of supplemental potassium, to be used during a dialysis treatment, wherein the slope is based on an area of the graph, which is defined by the length of time since the last dialysis treatment for the patient and the patient's historically recorded propensity to be affected by hypokalemia resulting from a dialysis treatment.

As shown in FIG. 2C, a graphical representation of the patient's scaled propensity to be affected by hypokalemia can be coordinated with the time since the patient last received a dialysis treatment, and the coordinate can be plotted on the graph. Depending upon which area of the graph the plotted coordinate lands, the physician can prescribe the corresponding suggested slope for gradually reducing the infusion of supplemental potassium over the course of the next treatment.

As shown in FIG. 2C, the physician may prescribe a very gradual slope for the reduction of supplemental potassium infusion, for any patient that has gone more than sixty (60) hours since his or her last dialysis treatment. For patients that have been evaluated and are determined to have a very low propensity to be affected by hypokalemia, and that have gone less than sixty (60) hours since their last dialysis treatment, a more aggressive or steeper negative slope can be prescribed to more rapidly decrease the infusion of supplemental potassium during the next dialysis treatment.

Although FIG. 2C shows the scaled propensity and the time since last treatment as a graphical representation, it is also to be understood that such data could be represented in a look-up table that is printed out or stored in a computer memory, arranged on a spreadsheet printed out or stored in a computer memory, stored in an external drive, stored on a readable medium, a combination thereof, or the like.

Figure 3:
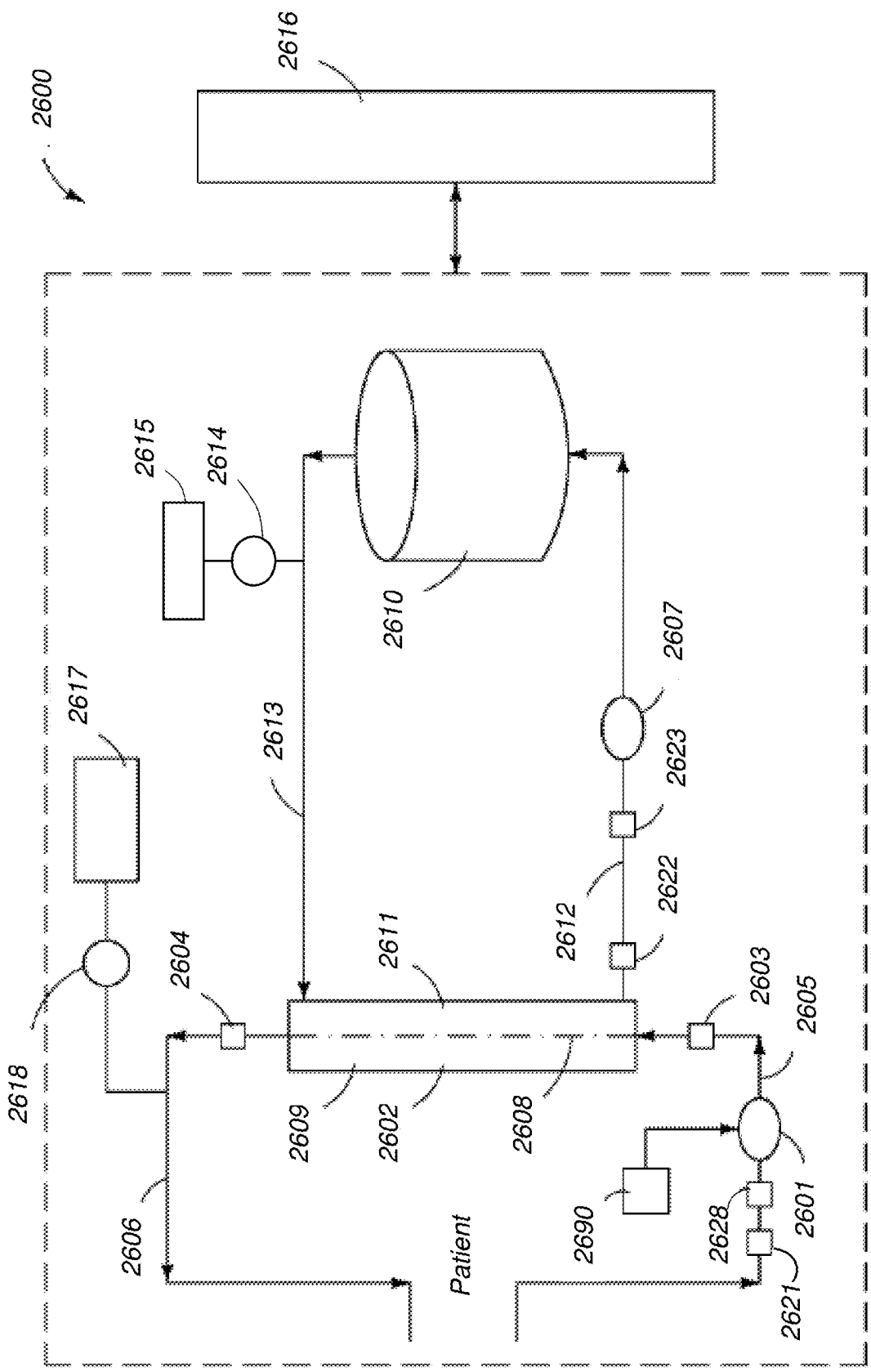
FIG. 3 is a functional block diagram of a multi-pass sorbent-based dialysis system including an electronic control unit, according to one or more embodiments of the present invention.

The system shown in FIGS. 1A and 1B is exemplary of a multi-pass dialysate regeneration system according to one or more embodiments of the present teachings. The disclosed embodiments can be used to provide dialysis treatments to a patient. FIG. 3 is a functional block diagram of another multiple-pass sorbent-based dialysis system according to one or more embodiments of the present invention, but which could also be configured as a single-pass system using one or more bags of fresh dialysate. Dialysis system 2600 employs a dialyzer cartridge 2602 comprising a high flux membrane to remove toxins from the blood both by diffusion and by convection. The removal of toxins by diffusion is accomplished by establishing a concentration gradient across the semi-permeable membrane by allowing a dialysate solution to flow on one side of the membrane in one direction while simultaneously allowing blood to flow on the other side of the membrane in opposite direction. To enhance removal of toxins using hemodiafiltration, a substitution fluid is continuously added to the blood either prior to the dialyzer cartridge (pre-dilution) or after the dialyzer cartridge (post-dilution). An amount of fluid equal to that of the added substitution fluid is "ultra-filtered" across the dialyzer cartridge membrane, carrying the added solutes with it.

Figure 4:
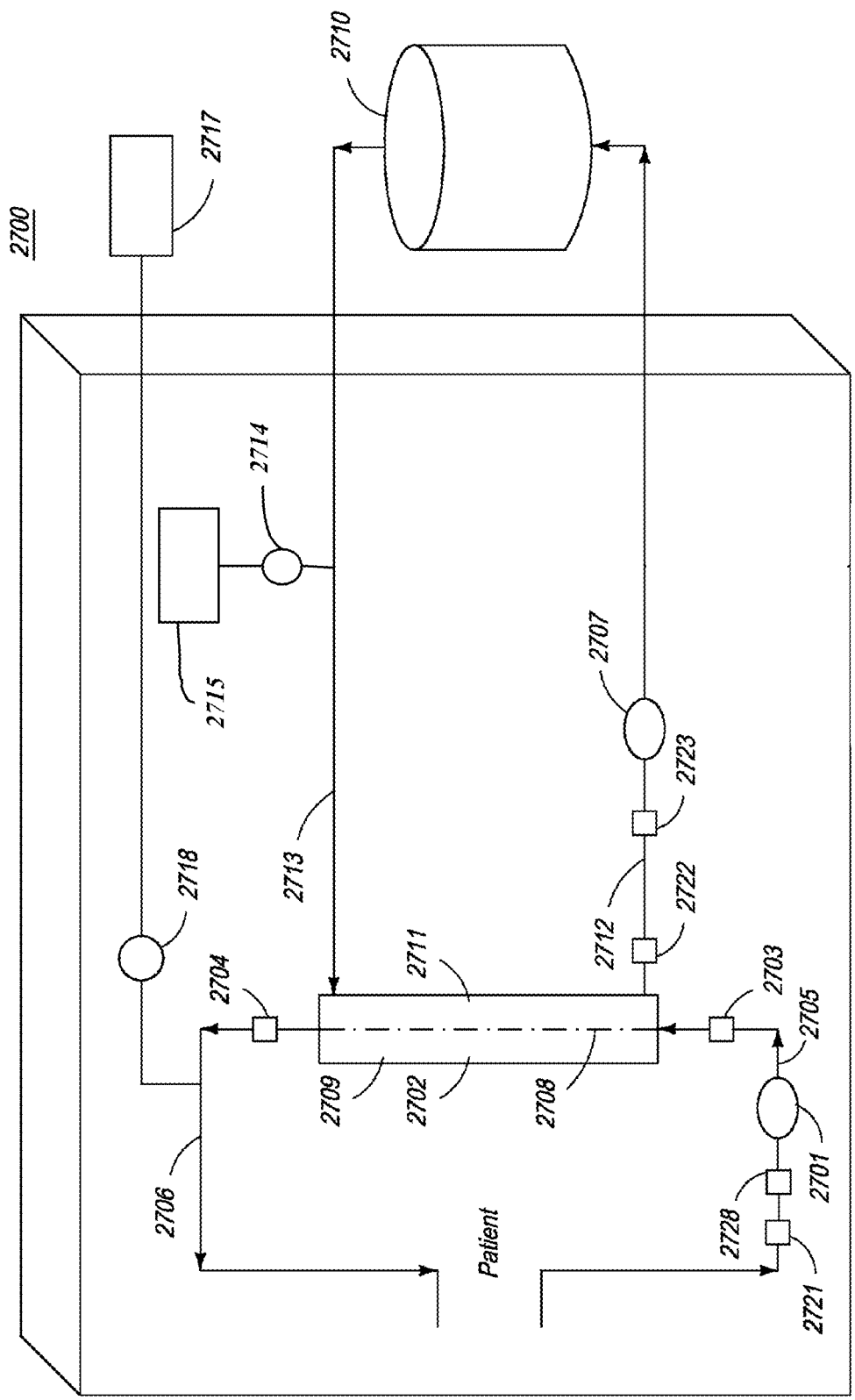
FIG. 4 is a functional block diagram of a multi-pass sorbent-based dialysis system in accordance with one or more embodiments of the present invention.

Referring to both FIGS. 3 and 4 simultaneously, blood containing toxins can be pumped from a blood vessel of a patient by a blood pump 2601, 2701 and transferred to flow through dialyzer cartridge 2602, 2702. Optionally, inlet and outlet pressure sensors 2603, 2604, 2703, 2704 in the blood circuit can be used to measure the pressure of blood both before it enters the dialyzer cartridge 2602, 2702 via the blood inlet tube 2605, 2705 and after leaving the dialyzer cartridge 2602, 2702 via the blood outlet tube 2606, 2706. Pressure readings from sensors 2603, 2604, 2628, 2703, 2704, 2728 are used as a monitoring and control parameter of the blood flow. A potassium sensor as disclosed herein is arranged in the form of a flow cell 2619. A patient's blood potassium concentration can be sensed, measured, and/or calculated by the sensor, for example, via processing by an electronic control unit 2616. Electronic control unit 2616 has a data processing unit in the form of a microprocessor, on which a data processing program (software) can run. A flow meter 2621, 2721 may be interposed in, or otherwise in pressure communication with, the portion of blood inlet tube 2605, 2705 that is located directly upstream from the blood pump 2601, 2701. The flow meter 2621, 2721 is positioned to monitor and maintain a predetermined rate of flow of blood in the impure blood supply line. A substitution fluid 2690 may be continuously added to the blood either prior to the dialyzer cartridge (pre-dilution) or after the dialyzer cartridge (post-dilution). The substitution fluid can comprise a solution of supplemental potassium, for example, consisting essentially of potassium in solution and being free of other minerals.

In both FIGS. 3 and 4, dialyzer cartridge 2602, 2702 comprises a semi-permeable membrane 2608, 2708 that divides the dialyzer 2602, 2702 into a blood chamber 2609, 2709 and a dialysate chamber 2611, 2711. As blood passes through the blood chamber 2609, 2709, uremic toxins are filtered across the semi-permeable membrane 2608, 2708 due to convective forces. According to one or more embodiments, additional blood toxins are transferred across the semi-permeable membrane 2608, 2708 by diffusion, primarily induced by a difference in concentration of the fluids flowing through the blood and dialysate chambers 2609, 2709 and 2611, 2711 respectively. The dialyzer cartridge used may be of any type suitable for hemodialysis, hemodiafiltration, hemofiltration, or hemoconcentration, as are known in the art. In one embodiment, the dialyzer 2602, 2702 contains a high flux membrane. Examples of suitable dialyzer cartridges include, but are not limited to, Fresenius® F60, F80 available from Fresenius Medical Care of Lexington, Mass., Baxter Conn. 110, CT 190, Syntra® 160 available from Baxter of Deerfield, Ill., or Minntech Hemocor HPH® 1000, Primus® 1350, 2000 available from Minntech of Minneapolis, Minn.

Dialysate pump 2607, 2707 can draw spent dialysate from the dialyzer cartridge 2602, 2702 and force the dialysate into a dialysate regeneration system 2610, 2710 and back into the dialyzer cartridge 2602, 2702 in a multiple pass loop, thus generating "re-generated" or fresh dialysate. Optionally, a flow meter 2622, 2722 can be interposed in the spent dialysate supply tube 2612, 2712, 2613, 2713 upstream from dialysate pump 2607, 2707, which monitors and maintains a predetermined rate of flow of dialysate. A blood leak sensor 2623, 2723 can also be interposed in spent dialysate supply tube 2612, 2712.

The multi-pass dialysate regeneration system 2600, 2700 of the present invention comprises a plurality of cartridges and/or filters containing sorbents for regenerating the spent dialysate. By regenerating the dialysate with sorbent cartridges, the dialysis system 2600, 2700 of the present invention requires only a small fraction of the amount of dialysate of a conventional single-pass hemodialysis device.

In one embodiment, each sorbent cartridge in the dialysate regeneration system 2610, 2710 is a miniaturized cartridge containing a distinct sorbent. For example, the dialysate regeneration system 2610, 2710 may employ five sorbent cartridges, wherein each cartridge separately contains activated charcoal, urease, zirconium phosphate, hydrous zirconium oxide and activated carbon. In another embodiment each cartridge can comprise a plurality of layers of sorbents described above and there can be a plurality of such separate layered cartridges connected to each other in series or parallel in the dialysate regeneration system. Persons of ordinary skill in the art would appreciate that activated charcoal, urease, zirconium phosphate, hydrous zirconium oxide and activated carbon are not the only chemicals that can be used as sorbents in the present invention. In fact, any number of additional or alternative sorbents, including polymer-based sorbents, can be employed without departing from the scope of the present invention.

While the current embodiment has separate pumps 2601, 2701, 2607, 2707 for pumping blood and dialysate through the dialyzer, in an alternate embodiment, a single dual-channel pulsatile pump that propels both blood and dialysate through the hemodiafiltration system 2600, 2700 can be employed. Additionally, centrifugal, gear, or bladder pumps can be used.

In one or more embodiments, supplemental potassium can be added to the dialysate in the dialysate tube 2613, 2713 using a volumetric micro-pump 2614, 2714 to increase the amount of potassium in the regenerated dialysate. The addition of supplemental potassium can be controlled by a micropump control signal generated by electric control unit 2616, for example, according to an input prescription. Supplemental potassium can be supplied from a solution reservoir 2615, 2715 that can be periodically refilled, as needed, via an inlet. A level sensor can be provided to monitor the amount of potassium solution that has been infused into the dialysate. The supplemental potassium solution can be a concentrated solution of potassium in water, for example, a solution of $K^+Cl^-$ in otherwise deionized water. Solutions having a potassium concentration of from about 300 milligrams per Liter (mg/L) to about 2,500 mg/L can be used, or solutions having concentrations of from 500 mg/L to 2,000 mg/L, or from 700 mg/L to 1,500 mg/L, or from 900 mg/L to 1,200 mg/L, or having a concentration of 1,000 mg/L. Supplemental potassium solutions having these concentrations of potassium, when added to dialysate at rates of from about one mL per minute to about 100 mL per minute, for example, from 10 mL per minute to 60 mL per minute, or from 20 mL per minute to 50 mL per minute, can supplement and increase the potassium concentration in the dialysate and thus provide or maintain relatively higher blood serum potassium concentrations during dialysis. Such relatively higher blood serum potassium concentrations can be useful, at least at the beginning of a dialysis treatment, to minimize the potential for hypokalemia developing in the patient, resulting from the dialysis.

The potassium concentration of the dialysate entering a dialyzer can be controlled by a combination of controlling the supplemental potassium solution concentration and controlling the rate of addition or infusion of the supplemental potassium solution into the dialysate stream. As mentioned above, electronic control unit 2616 comprises a microprocessor and monitors and controls the functionality of all components of the system 2600.

In one embodiment, dia-filtered blood exiting dialyzer cartridge 2602, 2702 is mixed with regulated volumes of sterile substitution fluid that is pumped into the blood outlet tube 2606, 2706 from a substitution fluid container 2617, 2717 via a volumetric micro-pump 2618, 2718. Substitution fluid is typically available as a sterile/non-pyrogenic fluid contained in flexible bags. This fluid can also be produced on-line by filtration of a non-sterile dialysate through a suitable filter cartridge rendering it sterile and non-pyrogenic.

Figure 5:
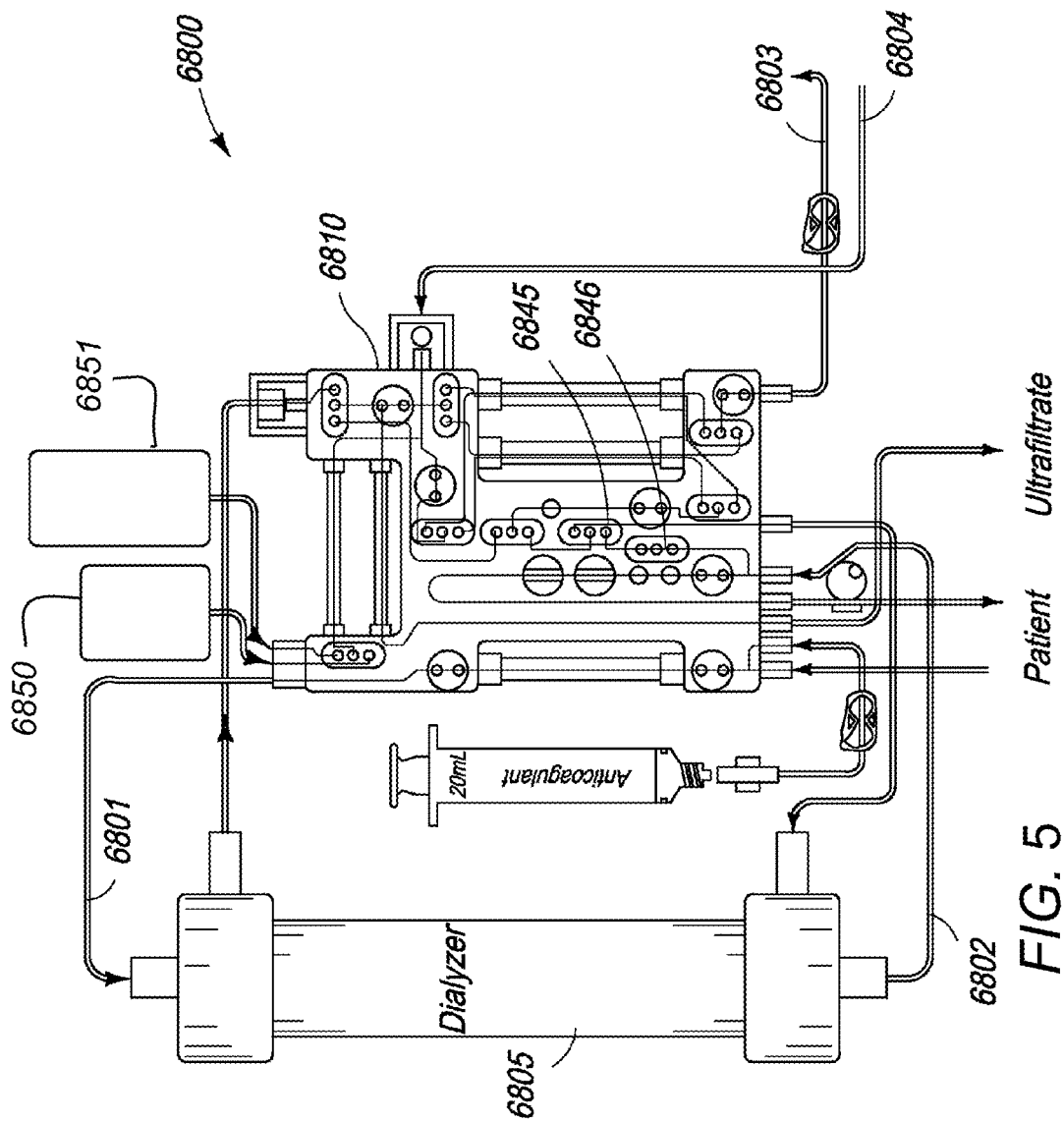
FIG. 5 is a schematic diagram of a treatment system comprising a compact manifold in a dialysis system, including two-way valves, to enable the control of flow through blood and dialysate circuits and to select a desired mode of operation, according to one or more embodiments of the present invention.

To enable a control flow through the blood and dialysate circuits and to select the desired mode of operation (hemodialysis or hemofiltration), the system can be provided with two-way valves, as described above. These valves can be actuated by a user to direct dialysate flow either through the dialyzer in one mode of operation or to deliver infusate grade dialysate flow directly to a patient, in a second mode of operation. These two-way valves can also be integrated with the compact manifold of the dialysis circuit. This is illustrated in FIG. 5. It should be noted that in FIGS. 5 and 6A-6C, for the purpose of clarity, corresponding elements are labelled with the same reference numerals.

Referring to FIG. 5, the extracorporeal blood processing system 6800 comprises a plastic molded compact manifold 6810 that encapsulates a plurality of molded blood and dialysate fluidic paths as well as a plurality of sensor areas, valves and fluidic pump segments. The dialyzer 6805 when connected to the arterial blood tube 6801 and venous blood tube 6802 of manifold 6810 completes the blood circuit of system 6800. In one embodiment, the dialyzer 6805 is disposable. Two lines—6803 and 6804, are used for circulating spent and fresh dialysate respectively. For operating the system 6800 in either of the two modes (hemodialysis and hemofiltration), a two-way valve 6845, and a backup two-way valve 6846 are provided.

Back up valve 6846 is employed because the dialysate used in hemodialysis is not sterile and not infusion grade while the fluid used in hemofiltration is. If operating in hemodialysis mode or if there is a leak or other failure of valve 6845, valve 6846 provides double protection against that fluid being pumped into the patient blood stream. Inclusion of backup valve 6846 allows the use of one manifold for both hemodialysis and hemofiltration safely. As noted above, two-way valves such as backup valve 6846 are composed of two single valves. In this case both one-way valves are in series and so by closing both ports of two-way valve 6846 double protection is afforded preventing dialysate from entering the blood stream. In an alternate embodiment a manifold can be made that is only intended for hemodialysis, having no connection between dialysis fluid circuit and blood circuit, thereby permitting valve 6846 to be safely eliminated.

Depending upon the patient's requirements, for example, as prescribed by a physician's prescription, desired quantities of concentrated potassium infusate solution from the potassium infusate container 6850 can be pumped, pulled, gravity-fed, or otherwise moved into the dialysate circuit passing through manifold 6810 so as to be added to the dialysate in the dialysate circuit. The concentrated potassium infusate solution can be a sterile solution that helps maintain a desired concentration of potassium in the dialysate, for example, at a level prescribed by a physician. A bypass valve and peristaltic pump, for example, can be provided to select the desired amount of concentrated potassium infusate solution and to ensure proper flow of the solution into the dialysate. Similarly, and depending upon a patient's requirements, as, for example, prescribed by a physician, a desired quantity of concentrated electrolytes solution from an electrolytes container 6851 can be pumped, pulled, gravity-fed, or otherwise moved into the dialysate circuit in manifold 6810. The concentrated electrolytes solution can be a sterile solution containing minerals, glucose, or the like, to help maintain minerals, including calcium and magnesium, in the dialysate at levels prescribed by a physician. The concentrated electrolytes solution can also contain potassium, but at a desired end-point concentration. Accordingly, dosing supplemental potassium such that an elevated concentration can be gradually reduced to a desired end-point concentration, can be enabled in accordance with the present teachings. A bypass valve and peristaltic pump can be provided to select the desired amount of concentrated electrolytes solution and to ensure proper flow of the solution into the dialysate. Through appropriate valving and plumbing, either or both the concentrated potassium infusate solution and the concentrated electrolytes solution can be pulled into the dialysate circuit from a single, common pump, for example, a peristaltic pump. The system comprises a control and computing unit that has a data processing unit, for example, a microprocessor, on which a data processing program (software) can run.

Figure 6A:
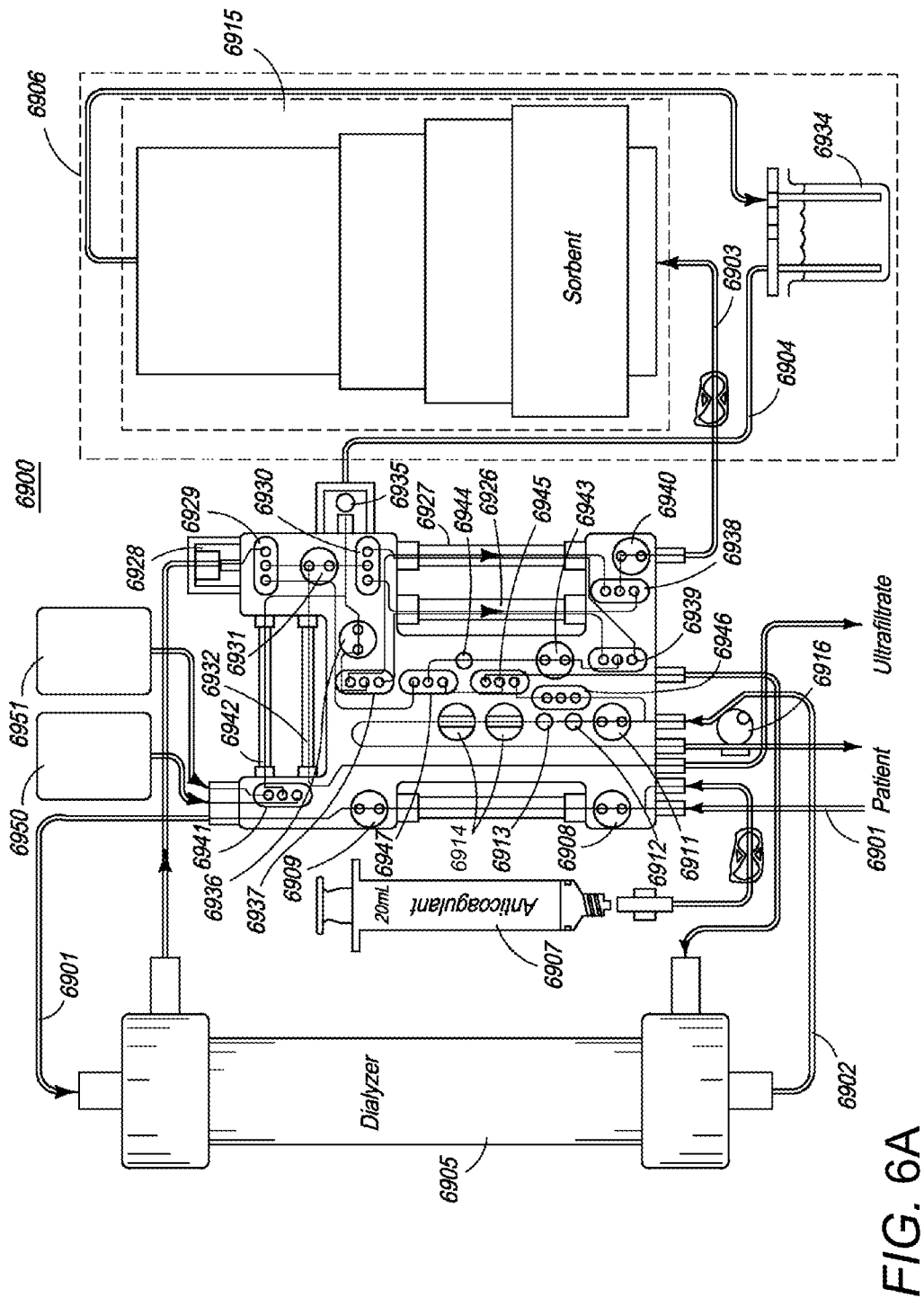
FIG. 6A is a schematic diagram of a circuit for hemodialysis/hemofiltration, according to one or more embodiments of the present invention, and including the compact manifold shown in FIG. 5.

FIG. 6A illustrates an exemplary circuit for a hemodialysis/hemofiltration system according to one or more embodiments of the present invention. Spent dialysate and fresh dialysate tubes 6903 and 6904, respectively, are connected to a dialysate regeneration system 6906 thereby completing the dialysate circuit of the system 6900. The dialysate regeneration system 6906 further comprises disposable sorbent cartridges 6915 and a reservoir 6934 to hold dialysate cleansed by cartridges 6915. Other components of the system shown in FIG. 6A are explained with reference to FIG. 6B, which shows an exploded view of the extracorporeal blood processing system 6900 configured to operate in hemodialysis mode. Corresponding elements in FIGS. 6A, 6B, and 6C have the same numbers.

Blood circuit 6920 comprises a peristaltic blood pump 6921 (FIGS. 6B and 6C) that draws a patient's arterial impure blood along the tube 6901 and pumps the blood through dialyzer 6905. A syringe device 6907 injects an anticoagulant, such as heparin, into the drawn impure blood stream. Pressure sensor 6908 is placed at the inlet of the blood pump 6921 while pressure sensors 6909 and 6911 are placed upstream and downstream of the dialyzer 6905 to monitor pressure at these vantage points.

As purified blood flows downstream from the dialyzer 6905 and back to the patient, a blood temperature sensor 6912 is provided in the line to keep track of temperature of the purified blood. An air eliminator 6913 is also provided to remove accumulated gas bubbles in the clean blood from the dialyzer. A pair of air (bubble) sensors (or optionally a single sensor) 6914 and a pinch valve 6916 are employed in the circuit to prevent accumulated gas from being returned to the patient.

The dialysate circuit 6925 comprises two dual-channel pulsatile dialysate pumps 6926, 6927. Dialysate pumps 6926, 6927 draw spent dialysate solution from the dialyzer 6905 and the regenerated dialysate solution from reservoir 6934 respectively. At the point where used dialysate fluid from the dialyzer 6905 enters the dialysate circuit 6925, a blood leak sensor 6928 is provided to sense and prevent any leakage of blood into the dialysate circuit. Spent dialysate from the outlet of the dialyzer 6905 then passes through the bypass valve 6929 to reach two-way valve 6930. A pressure sensor 6931 is placed between the valves 6929 and 6930. An ultrafiltrate pump 6932 is provided in the dialysate circuit, which is operated periodically to draw ultrafiltrate waste from the spent dialysate and store it in an ultrafiltrate bag 6933, which is emptied periodically.

As mentioned previously, spent dialysate is regenerated using sorbent cartridges. The dialysate regenerated by means of sorbent cartridge 6915 is collected in a reservoir 6934. Reservoir 6934 includes conductivity and ammonia sensors 6961 and 6962 respectively. From reservoir 6934, regenerated dialysate passes through flow restrictor 6935 and pressure sensor 6936 to reach a two-way valve 6937. Depending upon a patient's requirements, desired quantities of concentrated potassium infusate solution from container 6950 and/or concentrated electrolytes solution from container 6951 can be added to the dialysate. The concentrated potassium infusate solution is a sterile solution of potassium that, by a controlled infusion, helps initially maintain potassium in the dialysate at concentrations prescribed by a physician. The concentrated electrolytes solution is a sterile solution containing minerals and/or glucose that help maintain minerals like calcium and magnesium in the dialysate at levels prescribed by a physician. A bypass valve 6941 and a peristaltic pump 6942 are provided to select the desired amount of concentrated potassium infusate solution and concentrated electrolytes solution, and to ensure proper flow of the solutions into cleansed dialysate emanating from reservoir 6934.

The dialysate circuit comprises two two-way valves 6930 and 6937. Valve 6930 directs one stream of spent dialysate to a first channel of dialysate pump 6926 and another stream of spent dialysate to a first channel of dialysate pump 6927. Similarly, valve 6937 directs one stream of regenerated dialysate to a second channel of dialysate pump 6926 and another stream of regenerated dialysate to a second channel of dialysate pump 6927.

Streams of spent dialysate from pumps 6926 and 6927 are collected by two-way valve 6938 while streams of regenerated dialysate from pumps 6926 and 6927 are collected by two-way valve 6939. Valve 6938 combines the two streams of spent dialysate into a single stream that is pumped via pressure sensor 6940 and through sorbent cartridges 6915 where the spent dialysate is cleansed and filtered before being collected in reservoir 6934. Valve 6939 combines the two streams of regenerated dialysate into a single stream, which flows to two-way valve 6945 through a bypass valve 6947. A pressure sensor 6943 and a dialysate temperature sensor 6944 are provided on the dialysate flow stream to two-way valve 6945.

By reversing the state of two-way valves 6930, 6937, 6938 and 6939, pumps 6926 and 6927 are reversed in their action of one withdrawing dialysis fluid from dialyzer 6905 and the other supplying dialysis fluid to dialyzer 6905. Such reversal, when done periodically over short periods of time relative to the dialysis session, ensures that over the longer period of the entire dialysis session the dialysate fluid volume pumped into the dialyzer equals the amount of fluid pumped out and the only total fluid volume lost by dialysis circuit 6925 is that removed by ultrafiltrate pump 6932.

In hemodialysis mode, two-way valve 6945 allows the regenerated dialysate to enter dialyzer 6905 to enable normal hemodialysis of the patient's blood. One side of valve 6945 is closed leading to the patient's blood return line. Another two-way valve 6946 acts as a backup, keeping dialysate from entering the patient's blood line, with both ports of valve 6946 closed even if valve 6945 leaks or fails.

Figure 6B:
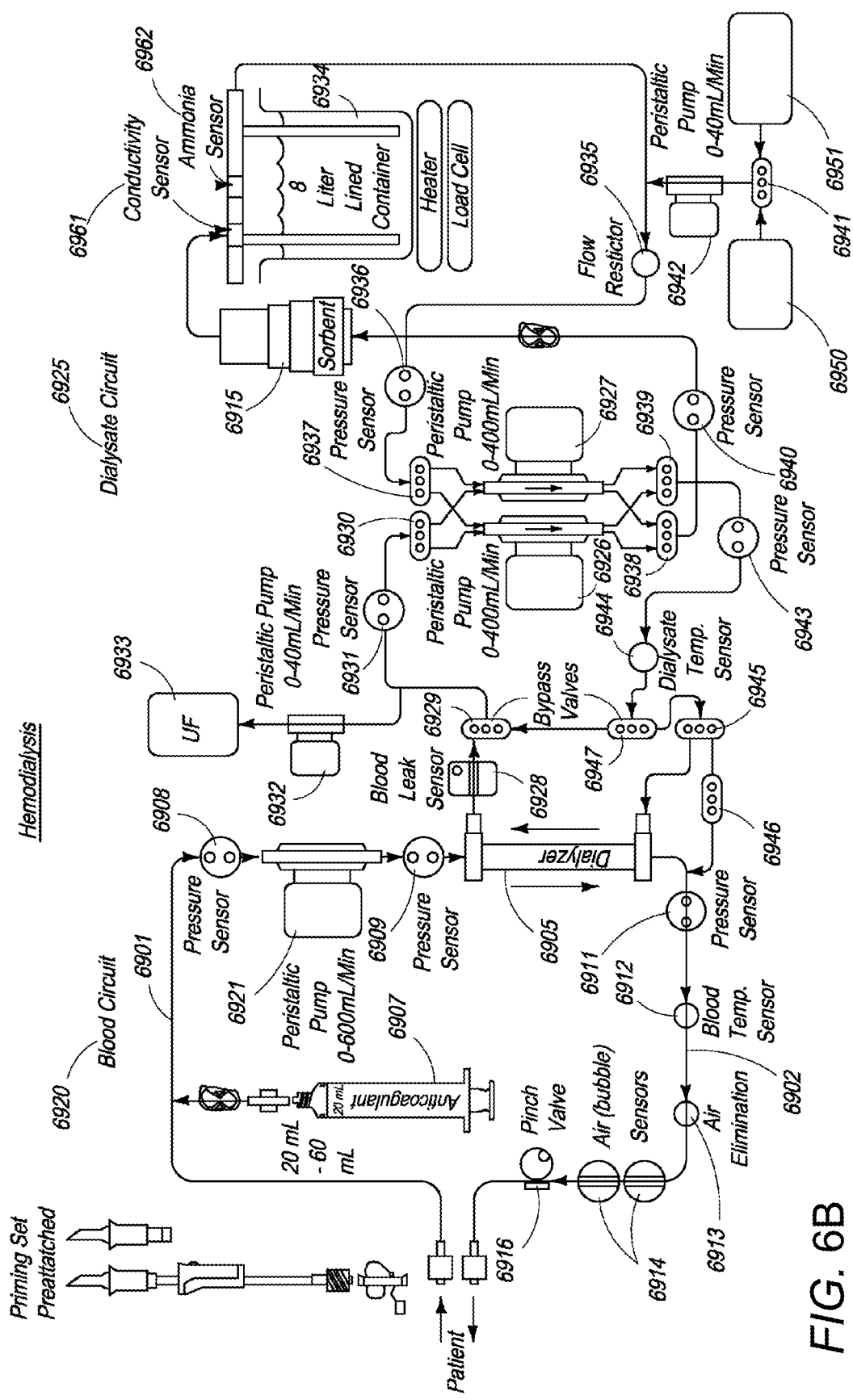
FIG. 6B is an exploded view of the extracorporeal blood processing system shown in FIG. 6A, configured to operate in hemodialysis mode.
Figure 6C:
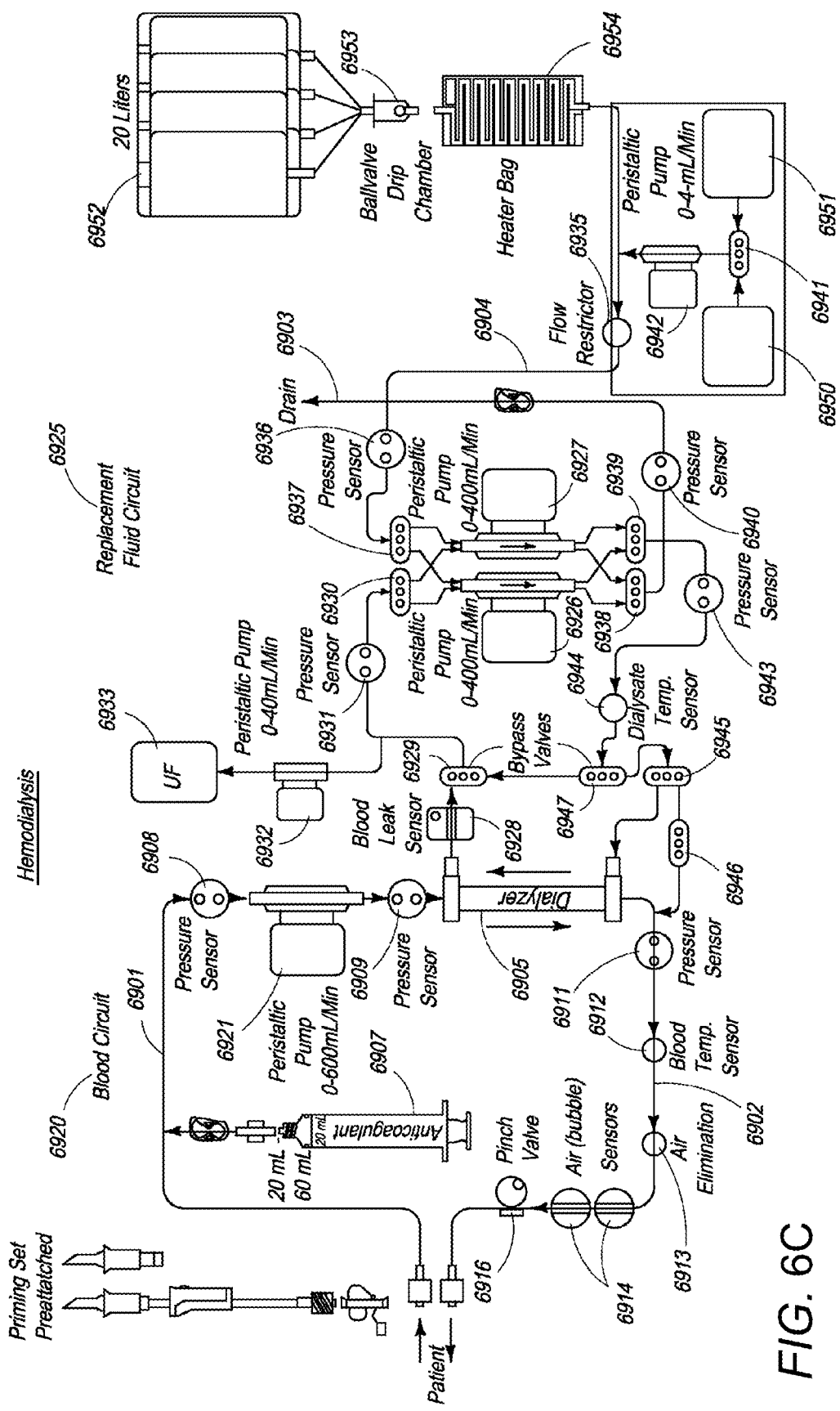
FIG. 6C is an exploded view of an extracorporeal blood processing system similar to that shown in FIGS. 6A and 6B, but configured for hemofiltration mode using a single-pass configuration and bag of fresh ultrapure dialysate.

Referring to FIG. 6C, in hemofiltration mode, two-way valve 6945 can be actuated to direct a stream of fresh ultrapure dialysate from reservoir 6952 through valve 6946, now with both ports open, to directly enter the stream of purified blood emanating from the dialyzer and flowing back to the patient.

It should be noted by persons of ordinary skill in the art that the backup two-way valve 6946 is a redundant safety valve to ensure that, in hemodialysis mode, failure of one valve 6945 does not result in infusion of regenerated dialysate directly into the patient. That is, both valves 6945 and 6946 are capable of being actuated by the system to allow fluid to be directed to the patient's venous blood line as a safety consideration. In some cases, the two-way back-up valve 6946 can be a single valve to allow or stop fluid flow.

It should be further noted by persons of ordinary skill in the art that valves as described in the description above are termed as "bypass" or "two-way" depending upon their use. Thus, valves are termed "bypass valves" when they bypass a component, such as the dialyzer. Otherwise they are termed "two-way valves" and simply direct the flow in at least two directions. The bypass and two-way valves can, however, be identical in construction.

The two-way valves can be fabricated as elastomeric membranes that are pressed against an orifice by a mechanism contained inside the dialysis machine to stop flow from having fluid contact with the rest of the fluidic circuit, as further discussed below.

Two-way valves 6945 and 6946 can be used for changing the mode of operation of the blood processing system. Referring to FIG. 6C, fluid flow in blood and dialysate circuits 6920 and 6925 is depicted. With the system operating in a hemofiltration mode or in a single-pass hemodiafiltration mode, spent dialysate tube 6903 is connected to a drain while fresh dialysate tube 6904 is connected to fresh, ultrapure, and injectable-grade dialysate in reservoirs 6952. Fresh dialysate from reservoirs 6952 passes through a ball-valve drip chamber 6953 and then passes through a heater bag 6954 to flow into fresh dialysate tube 6904. The rest of the elements and fluidic paths of the blood and dialysate circuits 6920, 6925 are similar to those of FIG. 6B, except that, in hemofiltration, fresh dialysate or replacement fluid is introduced into dialysate circuit 6925 as the spent dialysate is drained and not reused.

As shown in FIGS. 6B and 6C blood circuit 6920 can comprise a peristaltic blood pump 6921 that draws a patient's arterial impure blood along tube 6901 and pumps the blood through dialyzer 6905. An optional pump 6907 injects an anticoagulant, such as heparin, into the drawn impure blood stream or anticoagulant can be injected as a bolus into the patient at the start of a treatment. Pressure sensor 6908 is placed at the inlet of blood pump 6921 while pressure sensors 6909 and 6911 are placed upstream and downstream of dialyzer 6905. Purified blood from dialyzer 6905 is pumped through tube 6902 past a blood temperature sensor 6912, air eliminator 6913, and air (bubble) sensor 6914, and back to a vein of the patient. A pinch valve 6916 is also placed to completely stop blood flow if air is sensed by the bubble sensor 6914 in the line upstream of the pinch valve 6916, thereby preventing the air from reaching the patient.

The dialysate circuit 6925 comprises two dual-channel dialysate pumps 6926, 6927. Dialysate pumps 6926, 6927 draw spent dialysate solution from the dialyzer 6905 and fresh dialysate from reservoir 6934 (FIG. 6B) or reservoirs 6952 (FIG. 6C). Spent dialysate from the outlet of dialyzer 6905 is drawn through blood leak sensor 6928 and bypass valve 6929 to reach two-way valve 6930. Pressure sensor 6931 is placed between valves 6929 and 6930. An ultrafiltrate pump 6932 is operated periodically to draw ultrafiltrate waste from the spent dialysate and to store the ultrafiltrate waste in an ultrafiltrate bag 6933 (that is emptied periodically). Fresh dialysate from reservoirs 6952 (FIG. 6C) passes through flow restrictor 6935 and pressure sensor 6936 to reach two-way valve 6937.

Heater bag 6954 can provide a heating function to raise the temperature of the fresh dialysate sufficiently so that the temperature of the ultrafiltered blood going back to the patient from dialyzer 6905, or the overall temperature of the mixture of ultrafiltered blood from dialyzer 6905 and the fresh dialysate infused directly into the purified blood by actuating the valves 6945, 6946, is equivalent to the body temperature of the patient, thereby preventing any thermal shock.

Figure 6D:
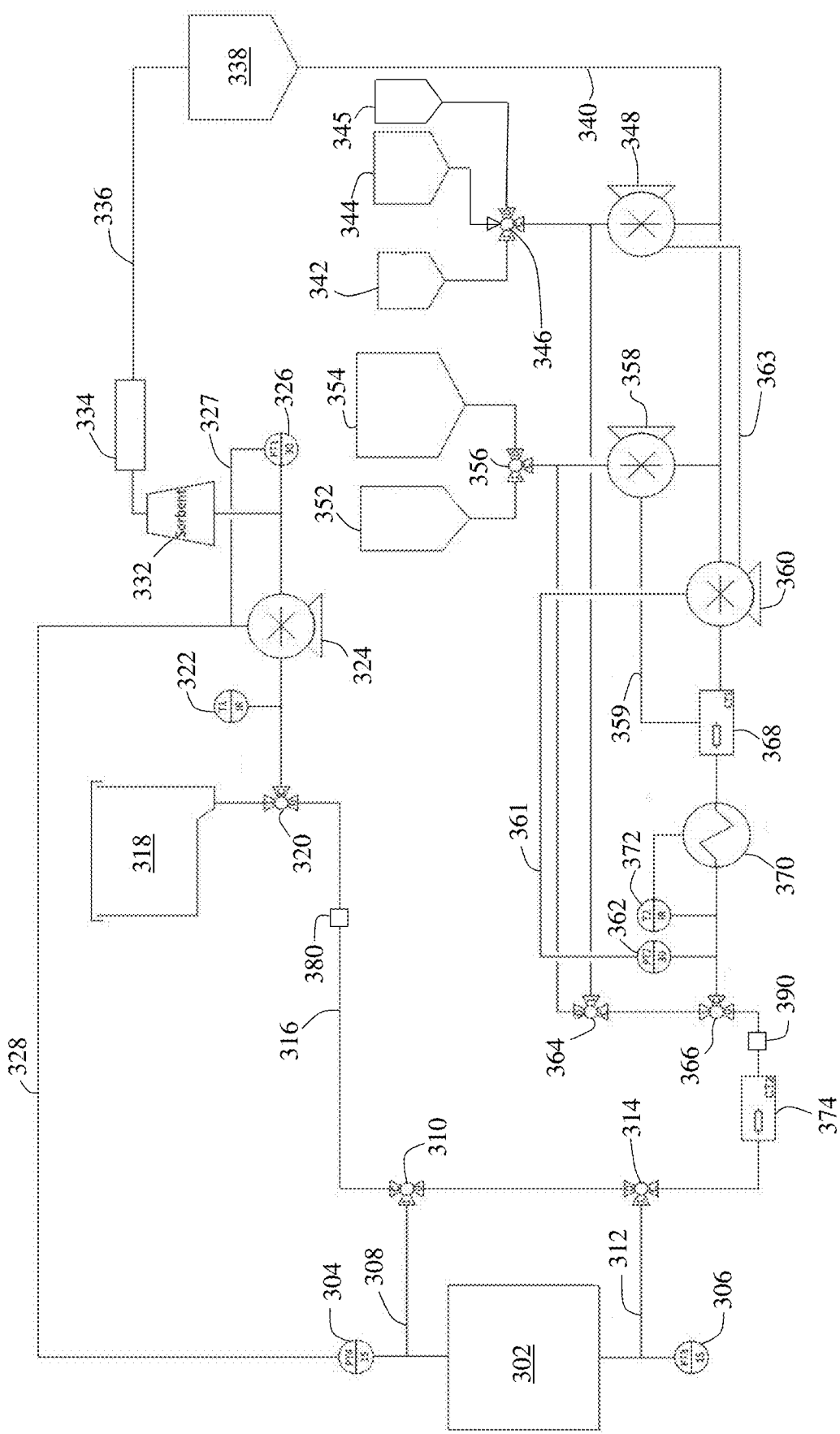
FIG. 6D is a schematic diagram of a dialysate circuit including a sorbent cartridge and potassium sensors, according to yet another embodiment of the present invention.

FIG. 6D is a schematic diagram showing a dialysate circuit that can be connected to, combined with, used in conjunction with, or used in place of a dialysate circuit for, an extracorporeal blood treatment machine 302, for example, the NxStage System One blood treatment machine available from NxStage Medical, Inc., of Lawrence, Mass. An incoming dialysate line 312, connected to a three-way valve 314, brings fresh or regenerated dialysate into blood treatment machine 302 where the fresh or regenerated dialysate can be used to treat blood flowing through an extracorporeal blood circuit. The fresh or regenerated dialysate can be directed through, for example, a dialyzer, through which also flows blood to be treated. A pressure sensor 306 is provided to monitor the pressure of the incoming dialysate in line 312. Subsequent to ion exchange contact with blood in blood treatment machine 302, used or spent dialysate can exit blood treatment machine 302 through a dialysate return line 308. A pressure sensor 304 can be operatively arranged to sense the pressure of used dialysate flowing through return line 308. Pressure sensor 304 can also act as a through-conduit in fluid communication with a pump control loop 328 leading to a first dialysate pump 324. Instead, or in addition, used dialysate exiting blood treatment machine 302 can pass through return line 308 and be directed, through a three-way valve 310, into a return conduit 316, through another three-way valve 320, and continue to dialysate pump 324. Along return conduit 316, a potassium sensor 380 can be disposed to sense the concentration of potassium in the used dialysate.

Three-way valve 310 and three-way valve 314 can be controlled by a controller or control unit (not shown) to shut-off dialysate conduit 312 and shut-off return line 308 to provide a bypass pathway that avoids blood treatment machine 302. The bypass pathway can be used, for example, in priming the dialysate circuit, further purifying the dialysate, or both. Three-way valve 320 can be controlled by the control unit to enable priming solution to be drawn by dialysate pump 324, from a prime tank 318 that can hold, for example, eight liters of a priming solution. The priming solution can thus be drawn into the dialysate circuit. A temperature sensor 322 can be provided to sense the temperature of the used dialysate or priming solution entering dialysate pump 324.

Dialysate pump 324 is configured to pump used dialysate or priming solution through a sorbent cartridge 332 for the purpose of regenerating used dialysate or purifying the priming solution. A pressure sensor 326 can be provided, in fluid communication with a fluid conduit 327 connecting dialysate pump 324 to sorbent cartridge 332, and can provide a bypass circuit for the purpose of limiting or controlling the flow of dialysate into and through sorbent cartridge 332, especially under exceedingly high-pressure conditions. Dialysate or priming solution that does pass through sorbent cartridge 332 is then directed through an ammonia (NH4+) sensor 334 before the sorbent cartridge-treated dialysate or priming solution flows through a reservoir conduit 336 and into a reservoir 338. Reservoir 338 can be in the form of a twelve-liter reservoir, in the form of two six-liter reservoirs, or the like. Regenerated dialysate, or purified priming solution, is pulled from reservoir 338, by a second dialysate pump 360 from which the fluid is pushed through a conditioning and temperature controller 368, through a heater 370, through a three-way valve 366, through a second potassium sensor 390, through a conditioning and temperature control and safety system 374, and to three-way valve 314. From three-way valve 314, the regenerated dialysate or priming solution can be directed through input conduit 312 and into blood treatment machine 302. Through the use of three-way valve 366 and other three-way valves 364, 346, and 356, the regenerated dialysate or priming solution can be further conditioned, including, for example, with supplemental potassium, before being directed through three-way valve 366 and toward three-way valve 314. Potassium sensor 390 can instead be incorporated into conditioning and temperature controller 368 and/or conditioning and temperature control and safety system 374.

Although fresh dialysate, regenerated dialysate, or priming solution can fill or partially fill the dialysate circuit, including reservoir 338, further operation of the circuit will hereafter be exemplified with reference to regenerated dialysate, for the sake of simplicity. Regenerated dialysate pushed from second dialysate pump 360 toward three-way valve 366 exerts pressure that can be sensed by a pressure sensor 362. Under conditions of exceedingly high pressure, pressure sensor 362 can act as a ball valve or similar device to enable a flow of regenerated dialysate therethrough and into a pump control loop 361 that leads back to second dialysate pump 360. The temperature of the regenerated dialysate pushed by second dialysate pump 360 can be measured or sensed by a second temperature sensor 372. A control signal sent from second temperature sensor 372 to the control unit can be used by the control unit to operate heater 370 to provide more or less heating of the regenerated dialysate depending upon the temperature sensed.

The temperature, the electrolytes concentrations, the pH, and other properties of the regenerated dialysate can be sensed by conditioning and temperature controller 368 and corresponding signals can be sent to control electronics, for example, the control unit. Based on the signals provided, the control unit can send control signals to a conditioning control pump 358 and a three-way valve 356 to control the infusion of a bicarbonate solution into the regenerated dialysate flowing through conduit 340. The bicarbonate solution can be generated, as needed, by controlling the supply of a concentrated bicarbonate solution from a one-liter reservoir 352, and dilution water from a four-liter reservoir 354, by control of three-way valve 356 and conditioning control pump 358. A pump control loop 359 is provided to return conditioned regenerated dialysate to conditioning control pump 358, depending upon the parameters sensed by conditioning and temperature control unit 368.

In addition to conditioning the regenerated dialysate with a bicarbonate solution, the regenerated dialysate can also be conditioned with a salt and dextrose solution, an electrolyte solution, and a potassium solution. A pump 348, herein referred to as electrolytes pump 348, can pull the various solutions through a four-way valve 346 and pump the resultant mixture of solutions into conduit 340 toward second dialysate pump 360. A pump-to-pump control loop 363 provides a fluid communication from pump 360 to pump 348 for the purpose of recirculating dialysate flow to pump 348, equalizing the fluid flow resulting from both pumps 360 and 348, and relieve overpressure.

Four-way valve 346 is in fluid communication with a 150 mL reservoir 342 containing a salt and dextrose solution, a 500 mL reservoir 344 containing an electrolytes solution, and a 100 mL reservoir 345 containing a supplemental potassium solution. Based on signals received from conditioning and temperature control unit 368, conditioning and temperature control and safety system 374, and at least one of potassium sensors 380 and 390, the control unit can send control signals to four-way valve 346 to control the mixing of the solutions from reservoirs 342, 344, and 345, and thus control the combined mixture of solutions entering electrolytes pump 348.

Yet another three-way valve 364 is provided that can be used in conjunction with a three-way valve 366 to recirculate dialysate for further conditioning with additional bicarbonate solution pulled through three-way valve 356, with additional electrolytes, salt, and sugar solutions pulled through four-way valve 346, or with both. The concentration of potassium in the regenerated dialysate, measured by potassium 390, can be controlled by controlling four-way valve 346 to enable more or less supplemental potassium to be pulled from reservoir 345 into the dialysate circuit. A target concentration of potassium in the regenerated dialysate can be based on the concentration of potassium sensed, in the used dialysate, by potassium sensor 380. Sensed potassium concentration from both potassium sensors 380 and 390 can be sent to the control unit and used by the control unit to regulate the infusion of supplemental potassium solution from reservoir 345.

The specific components that can be used for the various elements shown in FIG. 6D can include suitable components that are well-known to those of skill in the art. Many suitable components that can be implemented are described and shown in U.S. Patent Application Publication No. US 2011/0315611 A1 to Fulkerson et al., which is incorporated herein in its entirety by reference. Many of the components can be arranged in a cartridge or manifold, as described in US 2011/0315611 A1, and can similarly be arranged in a cartridge or manifold according to the present teachings. Pump 324 can be used as a cartridge-in pump under such circumstances.

Each of pumps 324, 360, 358, and 348 can independently be a non-occluding pump, an impeller pump, a centrifugal pump, an occluding pump, a peristaltic pump, or the like. Each of pumps 324 and 360 can independently provide a flow rate of from 50 mL/min to 500 mL/min, can provide a maximum pressure of 50 psig, and can provide accuracy that deviates by no more than 1 or 2 percent. Pump 358 can provide a flow rate of from 1 mL/min to 50 mL/min. Pump 348 can provide a flow rate of from 0.5 mL/min to 50 mL/min, and an accuracy that deviates by no more than 1 or 2 percent.

Temperature sensor 322 can comprise an infra-red temperature indicator. Exemplary indicators that can be used include the Omega, Smart-micro IR t/c temperature indicator no. OS35R5-100C-V5-12V that can indicate a maximum temperature of 100° C., provide an output of from 0 to 5 volts, and can run on 12-volt DC. Omega temperature indicators are available from OMEGA Engineering, Inc. of Norwalk, Conn. Temperature sensor 372 can comprise of the same type or same model of temperature indicator as sensor 322.

Heater 370 can comprise any suitable heating assembly known to those of skill in the art. The heater can be an in-line flow-through heater. Heater 370 can comprise any suitable heating assembly known to those of skill in the art. The heater can comprise an in-line flow-through heater. Heater 370 can be configured, for example, to provide a dialysate temperature change of up to 50° C. in dialysate flowing at a flow rate of up to 500 mL/min.

Conditioning and temperature controller 368 can include one or more indicators, provide an output voltage of from 0 to 10 volts, provide a pre-treatment range of from 5 to 15 mS/cm in the temperature range of from 5° C. to 50° C., and provide a treatment range of from 12 to 14.5 mS/cm in the temperature range of from 35° C. to 42° C. Conditioning and temperature control and safety system 374 can include an indicator, provide an output voltage of from 0 to 10 volts, and provide a treatment range of from 13 to 14 mS/cm in a temperature range of from 35° C. to 42° C.

Each of valves 310, 314, and 320 can independently be a three-way or triple-port valve having a maximum allowable working pressure of 50 psig. Each of valves 356, 364, and 366 can be a three-way or triple-port valve having a maximum allowable working pressure of 30 psig. Valve 346 is a four-way valve having a maximum allowable working pressure of 30 psig. Other suitable valves and pressure ratings can be used. Each valve can independently be an electromagnetically actuated valve, a solenoid valve, a plunger valve, or the like. Custom-made valves from Custom Valve Repair of New Castle, Pa. can be used. Valves available from Qosina of Ronkonkoma, N.Y., can be used. Many of the valves described and shown in U.S. Patent Application Publication No. US 2011/0315611 A1 can be used.

Each of pressure sensors 326 and 362 can independently comprise a pressure transducer having a pressure sensing range of from 0 to 30 psi, a pressure over-range protection value of 60 psi, an operating temperate range of from −28° C. to 54° C., and a compensated temperature range of from −1° C. to 54° C. Other suitable ranges and values can be used. Exemplary pressure transducers exhibiting such parameters include the Honeywell pressure transducer 1865-07G-KDN available from Honeywell, Morristown, N.J.

Each of pressure sensors 304 and 306 can independently have a pressure sensing range of from 0 to 15 psig, a pressure over-range protection value of 45 psig, an operating temperature range of from −28° C. to 54° C., a compensating temperature range of from −1° C. to 54° C., and an accuracy that deviates by no more than 2.5 percent. An exemplary pressure sensor exhibiting such parameters is the Honeywell pressure transducer 1865-03G-KDN, available from Honeywell, Morristown, N.J. Other suitable pressure transducers can be used.

FIGS. 7A and 7B are a cross-sectional side view and top view, respectively, of a flow cell 700 for sensing blood potassium concentration in an extracorporeal blood circuit, according to one or more embodiments of the present invention. Flow cell 700 comprises a body 702, a lid 704, a pair of electrodes comprising a sensing electrode 706 and a reference electrode 708, and a wire harness 710. Blood flowing through an extracorporeal blood tubing 712 enters the interior 714 of flow cell 700 through an inlet 716 and exits flow cell 700 through an outlet 718. Electrical leads from the electrodes are harnessed by wire harnesses 710 and are in electrical communication with ion selective electrode circuitry (not shown) as described herein. Signals from the electrodes are used to sense the blood potassium concentration in the blood flowing through the flow cell. The electrodes can comprise potassium permeable ion selective membranes.

Lid 704 can comprise catches 720 that engage with protrusions 722 on body 702 to lock lid 704 to body 702. Two release tabs 724 are provided to release lid 704 from body 702. Lid 704, including electrodes 706 and 708, can be sterilized and reused whereas flow cell body 702 can be made as a disposable component and can be protected by a temporary cover lid to keep interior 714 of flow cell 702 sterile until use. During use, electrodes 706 and 708 are connected to lid 704 and are aligned with through-holes in a top 726 of body 702. O-rings 728 and 730 are provided to seal top 726 of flow cell body while electrodes 706 and 708 protrude into interior 714 of flow cell 700. By being positioned in interior 714, electrodes 706 and 708 can be used to sense blood potassium concentration in blood flowing through flow cell 700. Electrical leads 746 and 748 electrically connect sensing electrode 706 and reference electrode 708, through wire harness 710, to ion selective electrode circuitry that can be fully encompassed by, a part of, or independent from the control and computing unit of the dialysis system. A control and computing unit is provided that as a data processing unit, for example, a microprocessor, on which a data processing program, for example, software, can run.

Figure 8:
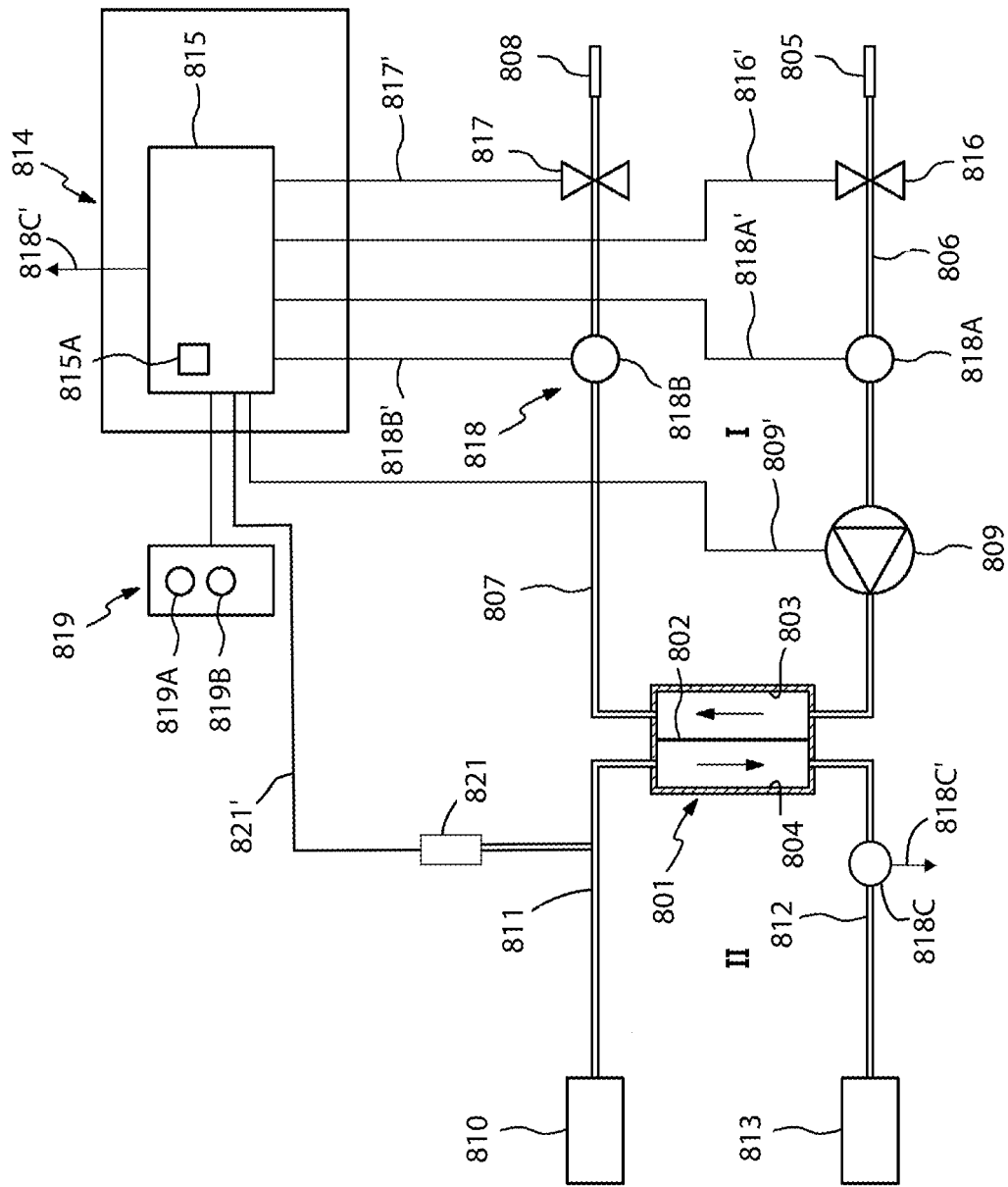
FIG. 8 is a schematic diagram showing yet another embodiment of the present invention, wherein a hemodialysis device is provided that has a blood treatment unit in the form of a dialyzer or filter that is divided into a blood chamber and a dialysate chamber by a semipermeable membrane, and wherein blood serum potassium concentration is regulated by supplemental infusion of potassium ions into dialysate.

FIG. 8 shows another embodiment of the present invention, wherein a hemodialysis device is provided that has a blood treatment unit in the form of a dialyzer or filter 801 that is divided into a blood chamber 803 and a dialysate chamber 804 by a semipermeable membrane 802. An arterial tube 806 is connected by means of an arterial puncture cannula 805 as a patient connection to a patient's fistula or shunt (not shown) and leads to an inlet to the blood chamber 803 of dialyzer 801. A venous tube 807 that is connected by means of a venous puncture cannula 808, as a patient connection to the patient's fistula or shunt, goes out from the outlet of the blood chamber 803 in dialyzer 801. A blood pump 809 is connected to arterial tube 806 and pumps blood in the extracorporeal blood flow circuit I. Blood pump 809 is preferably an occlusion pump, for example, a peristaltic pump. The arterial and venous tubes form the arterial and venous branches 806, 807, respectively, of the extracorporeal blood flow.

The dialysate flow circuit II through the dialyzer includes a dialysate source 810 to which a dialysate supply line 811 is connected that leads to the inlet for dialysate chamber 804 of dialyzer 801. A dialysate outlet line 812 leads from the outlet of dialysate chamber 804 of the dialyzer 801 to an outlet 813, for example, a drain or storage bag. A dialysate pump (not shown) is connected to dialysate outlet line 812.

The dialysis device is controlled by a central control and computing unit 814 that has a computer, microprocessor, or other processor that is programmed such that the steps required for controlling the individual components and for detecting and evaluating measured values are performed. In the present exemplary embodiment, a control and computing unit 815, in the form of a computer making up or being a part of a monitoring device, is a component of central control and computing unit 814. Either or both of central control and computing unit 814 and control and computing unit 815 can have a data processing unit, for example, a microprocessor, on which a data processing program (software) can run.

An arterial potassium sensor 818A is provided on arterial tube 806 downstream of the arterial cannula 805 and upstream of blood pump 809, and a venous potassium sensor 818B is provided on venous tube 807 upstream of venous cannula 808. The potassium sensors 818A and 818B, may each individually be any one of the potassium sensors disclosed and/or shown herein. An arterial cut-off unit 816, such as a valve, is provided on arterial tube 806 downstream of arterial cannula 805 and upstream of blood pump 809, and a venous cut-off unit 817 is provided on venous tube 807 upstream of venous cannula 808. The cut-off units 816 and 817, may be electromagnetically actuatable tube clamps. In principle, however, the arterial cut-off unit 816 may omitted.

The monitoring device can have, as shown, an alarm unit 819 that, in the present exemplary embodiment, is a component of the alarm unit for the blood treatment device. Potassium infusion rates, low potassium levels, or high potassium levels, can be trigger alarms and can indicate a need for action. Alarm unit 819 has a first signal generator 819A and a second signal generator 819B. The first signal generator 819A provides only a preliminary alarm, for instance only a visual signal, an indication on the screen of the machine, or a corresponding recording, while the second signal generator 819B provides an acoustic and/or visual and/or tactile alarm that is immediately perceivable.

For controlling the individual components and for detecting the measured values, the blood pump 809 is connected to central control and computing unit 815 via a control line 809', connected to alarm unit 819 via a control line 819', connected to the arterial and venous cut-off units 816 and 817, via control lines 816' and 817', and the arterial and venous potassium sensors 818A and 818B, via control lines 818A' and 818B'. The control and computing unit 815 is programmed such that, during the blood treatment, the arterial and venous serum potassium concentrations are measured continuously using signals generated by potassium sensors 818A and 818B. Pressure sensors (not shown), can also be included, for example, to monitor one or more vascular accesses.

Blood serum potassium concentration can be control during a blood treatment session by sensing, measuring, and/or calculating serum blood level values using potassium sensors 818A and 818B. As blood serum potassium concentrations pre-dialyzer, measured in arterial tube 806 are compared with blood serum potassium concentrations post-dialyzer, measured in venous tube 807, the central control and computing unit 805 regulates the infusion of supplemental potassium into the dialysate flowing through dialysate line 811 for exchange with blood in dialyzer 801. The central control and computing unit 805 regulates the infusion of supplemental potassium into the dialysate flowing through dialysate line 811 by sending a control signal via a control line 821' to a potassium supply device 821 comprising a container containing a supply of potassium ions, for example, a potassium salt solution, and a syringe pump driven by a stepper motor and configured to drive or otherwise force the supply of potassium ions into the stream of dialysate flowing through hose 811 and into dialyzer 801. A one-way valve can be provided to prevent back-flow of dialysate toward potassium supply device 821. The stepper motor and syringe pump are designed to receive control signals from the control and computing unit 815 or from another central, or separate, computer or processor, to control the addition of supplemental potassium into the dialysate, based on signals received from potassium sensors 818A and 818B.

If a fault is suggested and an alarm signal is generated, the control and computing unit 815 generates a control signal for the arterial and venous cut-off units 816 and 817 so that the cut-off units can be closed. Thus, the arterial and venous lines 806 and 807 can be completely closed-off from the patient in the event of a potassium level-related emergency or warning. The control and computing unit 815 can further generate a control signal for alarm unit 819 so that second signal generator 819B can provide a preferably acoustic alarm. After the acoustic alarm, medical staff can take the required measures.

During verification of a potassium level-related fault, the control and computing unit 815 continuously monitors whether a certain time interval that is prespecified by a timing unit element, has elapsed. Once the time interval has elapsed, the arterial and venous tube clamps 816 and 817 are automatically closed for safety reasons. This ensures that it is only possible to verify the fault and continue the blood treatment within narrow temporal limits.

According to various embodiments, a potassium sensor 818C can instead, or additionally, be used, as a sensor for providing signals to be evaluated and/or considered by control and computing unit 815 in the regulation of potassium supply device 821. The level or concentration of potassium in spent dialysate, or ultrafiltrate, passing through used dialysate tube 812, can be sensed, measured, and/or calculated to provide or be used in providing a control signal to regulate operation of potassium supply device 821. The control signal sent from potassium sensor 818C to regulate operation of potassium supply device 821 can be transmitted along control line 818C', or wirelessly, to control and computing unit 815 and/or to central control and computing unit 814, wherein the control signal can be processed and used to regulate the infusion of supplemental potassium from potassium supply device 821 to fresh dialysate hose 811.

Figure 9:
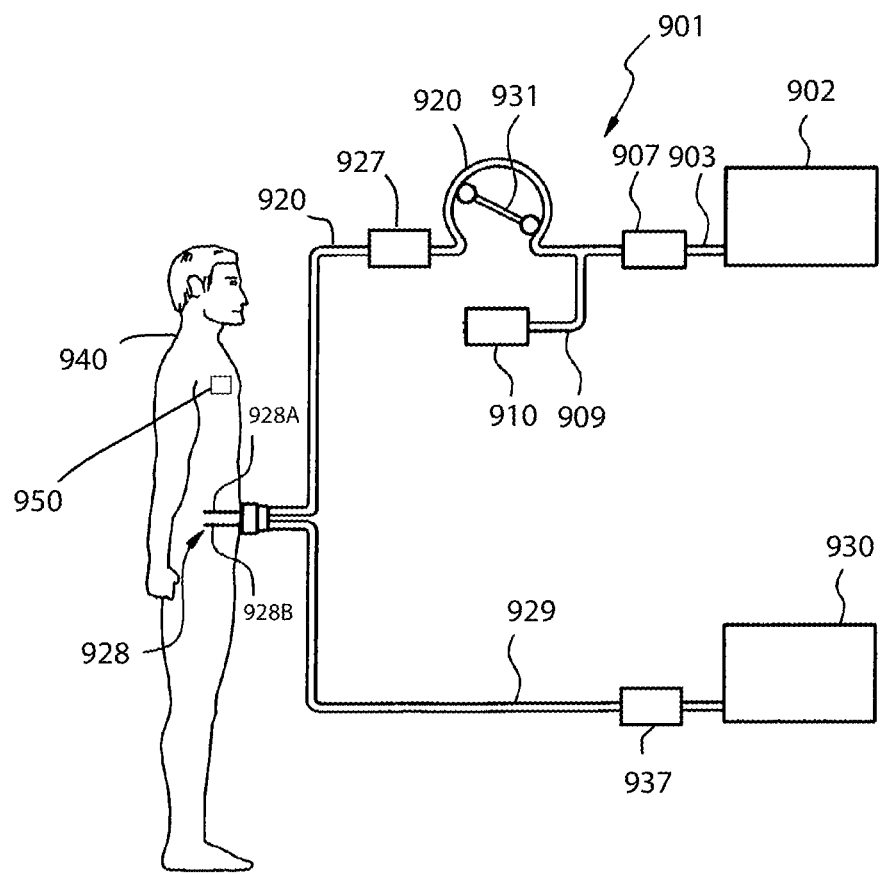
FIG. 9 is a schematic representation of an apparatus for peritoneal dialysis that includes a potassium supply device comprising a syringe pump driven by a stepper motor and configured to drive a supplemental supply of potassium ions into a stream of peritoneal dialysis solution.

FIG. 9 shows, in a very simplified schematic representation, an apparatus for peritoneal dialysis, in which a hose set 901 includes a branch line 909 that can be permanently attached to, or dis-connectable from, a supplemental potassium supply device 910 comprising a container containing a supply of potassium ions, for example, a potassium salt solution, and a syringe pump driven by a stepper motor and configured to drive or otherwise force the supply of potassium ions into the stream of peritoneal dialysis solution flowing through hose 920 and into the peritoneal cavity of a patient 940. The stepper motor and syringe pump are designed to receive control signals from a central or separate computer or other processor to control the addition of supplemental potassium into the peritoneal dialysis solution based on signals received from potassium sensors 907, 927, and 937, which signals are processed by the central computer or other processor. The central computer has a data processing unit, for example, a microprocessor, on which a data processing program (software) can run.

A peristaltic pump 931 pulls peritoneal dialysis solution from a supply bag 902, and pulls supplemental potassium supplied from supplemental potassium supply device 910. Peristaltic pump 931 pushes the resulting solution through hose portion proper 920 from peristaltic pump 931, through potassium sensor 927, and into the peritoneal cavity of patient 940.

Hose set 901 has a free end 903 connected to a supply bag 902 and can comprise a luer fitting, a threaded screw and threaded nut connector, a compression fitting, or another coupler, to connect free end 903 to supply bag 902. Free end 903 is also connected to, or passes through, a first potassium sensor 907 that can be provided to sense the potassium concentration in the peritoneal dialysis solution. First potassium sensor 907 can be omitted from use or inclusion, for example, if the concentration of the potassium supply in bag 902 is known, or for any other reason. A second potassium sensor 927 can be provided to sense the potassium concentration in the peritoneal dialysis solution after mixing with any supplemental supply of potassium but prior to infusion into the peritoneal cavity. The second potassium sensor 92 may also, or instead, be omitted from use or inclusion.

A first lumen 928A of a double-lumen peritoneal catheter 928 is provided for supplying peritoneal solution into the peritoneal space or for carrying away the solution from the peritoneal space of the patient. Double-lumen peritoneal catheter 928 also comprises or is connected to a second lumen 928B, for example, designed as part of peritoneal catheter 928. A hose line 929 is permanently or dis-connectably connected to second lumen 928B and also to a bag 930 for collecting used or spent peritoneal solution.

As shown in FIG. 9, an electrocardiogram (EKG) signal, sensed by EKG lead 950 on patient 940, can be processed by a central or separate computer or other processor to provide an additional or alternative control signal for regulating and/or controlling supplemental potassium supply device 910 and the addition, through branch line 909, of supplemental potassium into the peritoneal dialysis solution. As described below with reference to FIGS. 15 and 16, the electrocardiogram signal sensed and transmitted from EKG lead 950 can be, or include, a T wave, and the T wave can be digitally analyzed or processed to accurately estimate blood serum potassium in the patient. A wire, control line, or other signal transmitting device or system (not shown) can be attached to and extend from EKG lead 950, or a wireless system can be used, to transmit the electrocardiogram signal sensed to the central or separate computer or other processor. The central or separate computer can have a data processing unit, for example, a microprocessor, on which a data processing program (software) can run.

Sensed potassium concentration signals can be signal-processed, if desired or needed, so as to be interpreted and interrogated. Based on incoming and outgoing concentrations of potassium, with respect to the patient's peritoneal cavity, adjustments can be made, for example, to maintain a slow, uniformly consistent decrease in potassium concentration in the effluent to be collected in bag 930, over a portion of, or the entire, treatment. Rather than a linear uniformly consistent decrease, curves of desired potassium reductions over a treatment period can be followed, and the treatment parameters can be controlled based on sensed, measured, and/or processed potassium concentration signals. Curves of rates of potassium concentration reduction over time, that have been standardized, made into sets of standards, or otherwise relied upon can be followed to ensure proven safe treatment methods that reduce potassium serum concentrations safely, efficiently, yet at rates that reduce or eliminate risks of hypokalemia and shock effects associated with sudden and drastic reductions in serum potassium as might be experienced from overly aggressive and/or fast treatment methods.

Figure 10:
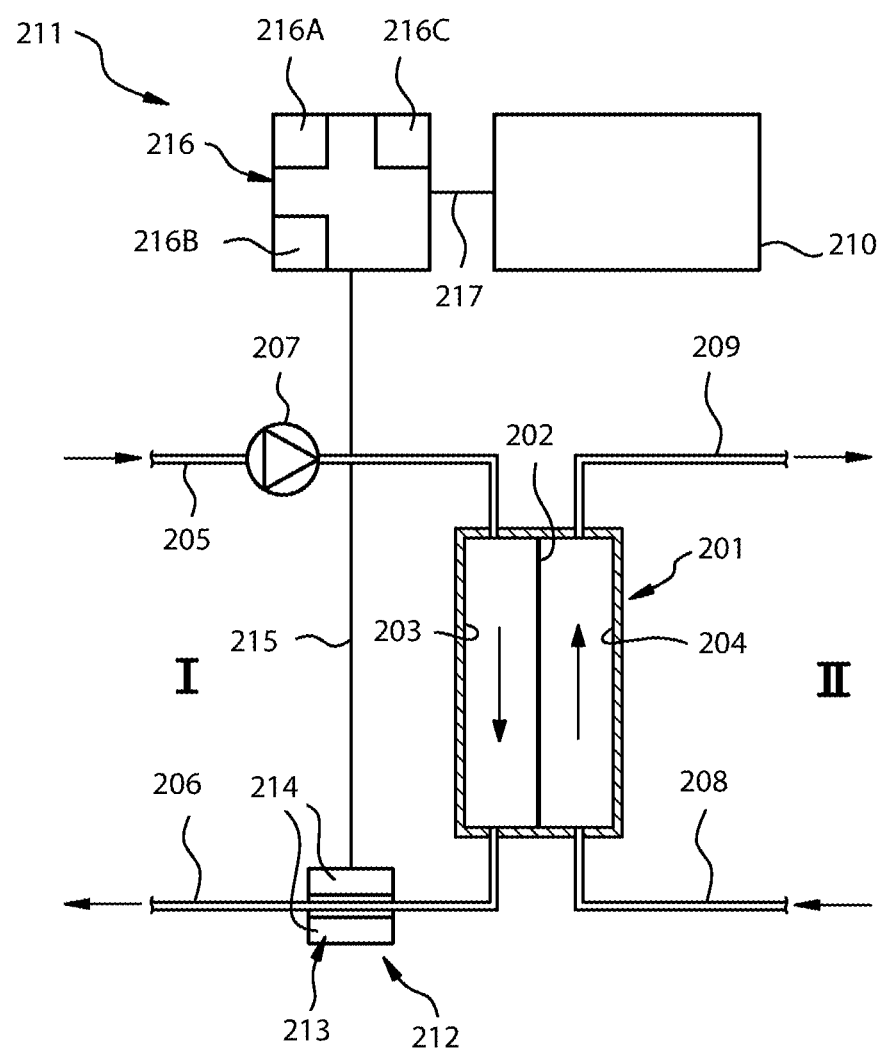
FIG. 10 is a representation of an apparatus for the extracorporeal blood circulation with a device for detecting blood serum potassium, seen in a very simplified and schematic depiction.

FIG. 10 shows the components for operating a blood serum potassium detection apparatus in an extracorporeal blood treatment, particularly in a dialysis device, illustrated in a very simplified schematic depiction. The extracorporeal blood treatment apparatus includes an exchange unit, for example, a dialyzer or filter 201, that is subdivided into a blood chamber 203 and a dialysis fluid chamber 204 by a semi-permeable membrane 202. An arterial blood supply line 205 leads from a patient to the blood chamber of dialyzer 201, while a venous blood return line 206 branches off from the blood chamber and leads to the patient. A blood pump 207 that is disposed in the arterial blood line 205 pumps the blood through an extracorporeal blood circuit I.

The dialysate fluid system II of the dialysis device is only partially shown in the drawing. It comprises a dialysis fluid supply line 208 leading to the dialysis fluid chamber 204 and a dialysis fluid discharge line 209 that branches off from the dialysis fluid chamber 204 of the dialyzer 201.

The arterial and venous blood lines 205, 206 are hose lines that are at least partially transparent with respect to electromagnetic radiation, particularly light. The blood treatment apparatus includes a central control unit 210 that controls the individual components, for example blood pump 207. The apparatus 211 for determining the blood serum potassium can be a structural component of the blood treatment apparatus, such that it can utilize components that are parts of the blood treatment apparatus, for example, the same central control and computing unit, computer, or other processor. The central control and computing unit can have a data processing unit, for example, a microprocessor, on which a data processing program (software) can run.

The apparatus 211 for detecting blood serum potassium includes a measuring unit 212 comprising a unit 213 into which a hose line of the extracorporeal blood circuit can be fitted, particularly, venous blood line 206. Measuring unit 212 comprises a transmitter and receiver unit 214 for coupling radiation in and out.

A data line 215 connects measuring unit 212 to a computing and analyzer unit 216, for example, comprising a central processing unit (CPU) including a memory. The computing and analyzer unit 216 is able to exchange data with a central control unit 210 of the blood treatment apparatus via a signal line 217. Either or both of computing and analyzer unit 216 and central control unit 210 can have a data processing unit, for example, a microprocessor, on which a data processing program (software) can run.

Figure 11A:
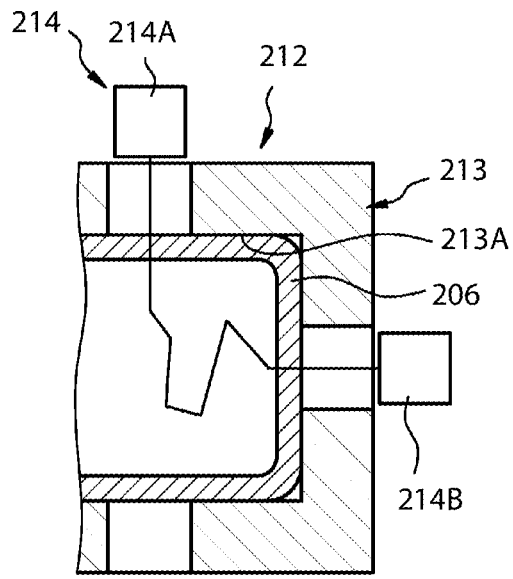
FIG. 11A is a representation of a partial view of a measurement unit of an apparatus for detecting blood serum potassium with a transmitter and a receiver for detecting scattered radiation, seen in a simplified depiction.
Figure 11B:
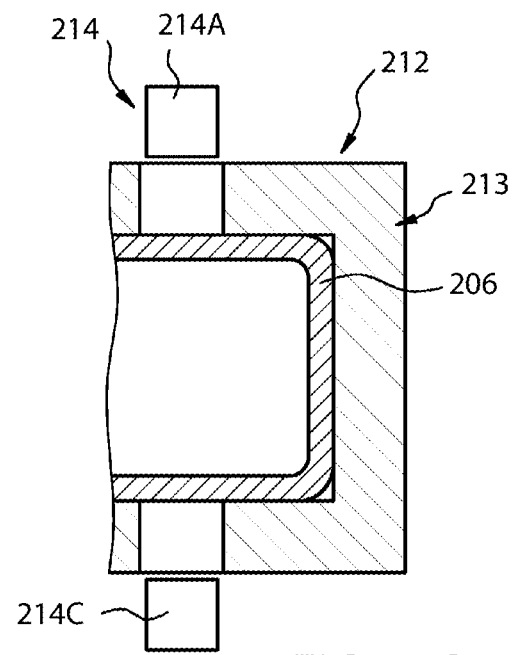
FIG. 11B is a representation of a partial view of the measurement unit with a transmitter and a receiver for detecting transmitted radiation, seen in a simplified depiction.

FIG. 11A shows a partial view of measuring unit 212, seen as a simplified cut representation. Measuring unit 212 includes a unit 213 with a receptacle 213A into which a blood line such as venous blood line 206 is clamped. The receptacle 213A includes four flat contact surfaces that are disposed at right angles relative to each other, and the hose line rests there against. FIG. 11A depicts only a single transmitter 214A and a single receiver 214B of transmitter and receiver unit 214. The radiation that is emitted by transmitter 214A passes through the hose line and into the blood that flows in the hose line 206, wherein the radiation emerging from the blood traverses through the hose line and is directed to receiver 214B. Due to the fact that the axes of the transmitter and receiver 214A, 214B are disposed at a right angle with respect to one another, the receiver receives the scattered radiation. For the detection of the transmitted radiation, the transmitter and the receiver 214A, 214C are disposed opposite each other on a shared axis, as depicted in FIG. 11B.

Figure 11C:
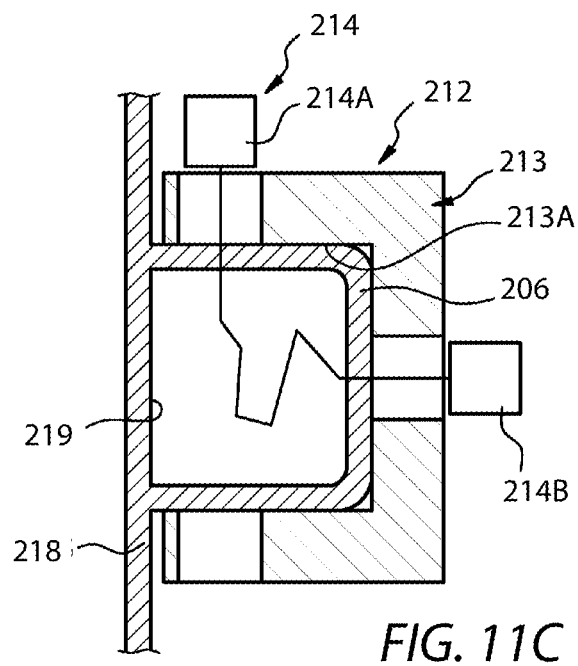
FIG. 11C is a representation of a partial view of an alternate embodiment of the measurement unit with a transmitter and a receiver for detecting scattered radiation, seen in a simplified depiction.

FIG. 11C shows an alternate embodiment of measuring unit 212 that is intended for a blood cartridge 218, wherein the blood flows through a blood channel 219, not through a hose line. Blood channel 219 is configured inside the cartridge. The part of the blood cartridge 218 forming channel 219 is made of a transparent material, for example, polycarbonate. Measuring unit 212 includes, for example, unit 213 and unit 213 is open on one side such that cartridge 218 can be fastened therein or that can otherwise be fastened to the cartridge. Measuring unit 212 and cartridge 218 thus constitute separate units, wherein measuring unit 212 is a component of the blood treatment apparatus and cartridge 218 can be exchanged and made disposable.

Figure 12:
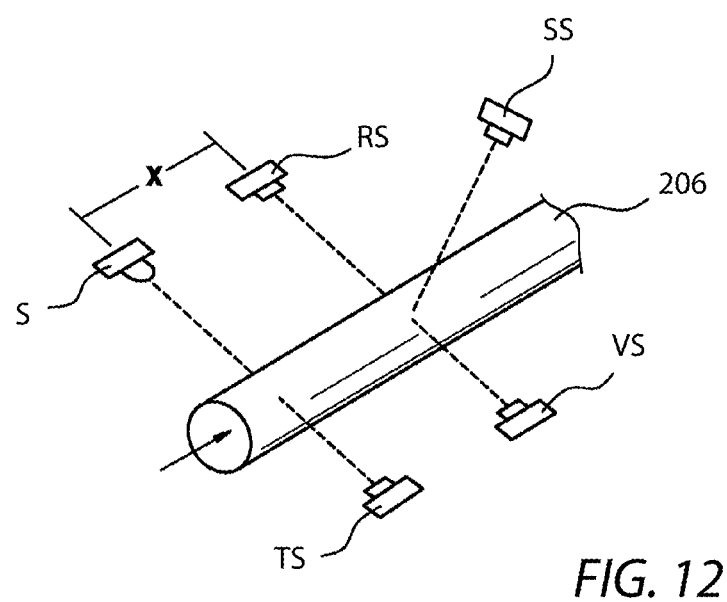
FIG. 12 is a representation of a depiction of a principle as embodied in the transmitting and receiving units for measuring the radiation according to different measuring methods.

FIG. 12 shows a representation of the principle that is embodied in a measuring apparatus with a transmitter and receiver unit 214 comprising a plurality of transmitters and receivers to be able to determine the blood serum potassium value by a variety of different measuring methods. Blood flows inside a transparent blood hose line such as venous line 206, in unit 213, and is clamped in unit 213 of the device for determining blood serum potassium (not shown in FIG. 12). The measurement apparatus for the transmission measurement includes a transmitter S and a receiver that are disposed on both sides of the hose line on a shared axis, facing each other. The receiver for the detection of the transmitted radiation is designated as TS. The axis of the transmitter S and receiver TS extends at a right angle relative to the longitudinal axis of hose line 206. Irradiation or light emitted from transmitter S, which propagates in the direction of the axis and impinges on blood flowing inside the hose line, is received by the receiver TS. The receiver TS supplies a measured signal that is proportionate to the intensity of the light and that is analyzed in the computing and analyzer unit 216. Lambert-Beer's law describes the relationship between the intensity of the incoming and emerging light. By selecting an appropriate transmitter and receiver pair, the blood serum potassium value can be calculated in computing and analyzer unit 216. For example, by using an ultra-violet (UV) transmitter and a UV receiver, an optical system for measuring UV absorbance can be used to measure blood serum potassium. By using a near infrared (NIR) transmitter and an NIR receiver, an NIR spectroscopy system for measuring an NIR spectrum can be used to determine a blood serum potassium value. By using a laser transmitter and a spectroscopic receiver, a laser-induced breakdown spectroscopy (LIBS) system can be used to measure blood serum potassium. None of these exemplary systems requires direct fluid contact with the blood to determine blood serum potassium relative values or exact measurements.

For the detection of scattered radiation (scattered light measurement), the measurement apparatus includes three further receivers as shown in FIG. 12. The receiver for the detection of the backward scatter (reflection) is designated as RS, the receiver for detecting the forward scatter is designated as VS, and the receiver for detecting the lateral scatter is designated as SS. The receivers RS and VS are disposed at the distance x relative to the transmitter S and receiver TS for the transmission measurement. The transmitter S and the receiver TS for the transmission measurement and the receiver RS and VS for the detection of the backward scatter and forward scatter are arranged inside a plane through which the longitudinal axis of the hose line 206 extends. The receiver RS for detecting the reverse scatter, the receiver VS for detecting the forward scatter, and the receiver SS for detecting the lateral scatter are arranged inside a plane that is perpendicular relative to the former plane. For the detection of the lateral scatter, the spacing x can also be zero.

The wavelength of the radiation that is emitted by the transmitter S, particularly the emerging light, can be in any suitable wavelength range. For some detection systems, the radiation is not in the visible range of 380 nm to 780 nm. The transmitter can comprise an LED, and OLED source, or the like. The transmitter can be a narrow-band LED source, for example, having a peak wavelength that is at 805 nm. The transmitter can comprise a laser source, an incandescent source, a fluorescent source, a quantum dot source, or the like. The receivers can be photodiodes, charge-coupled devices, or the like.

The blood serum potassium value can be determined by two different measuring methods. For example, the first measuring method can include a reflection measurement and the second measuring method can include a transmission measurement. The computing and analyzer unit 216 can calculate the difference between the value measured by the reflection measurement and the value measured by the transmission measurement, wherein conclusions as to the amount of potassium in the blood serum are drawn based on the difference of the two measured values. Conclusions that increased amounts of potassium are present can be based on an increase of this difference. An equation residing in the computing and analyzer unit 216, that describes the dependent relationship of the difference of the values and the amount of blood serum potassium, can be used for calculating the amount of potassium as a function of the difference of the measured values.

The amount of potassium measured, sensed, calculated, or determined can be represented on a display unit 216B of device 211 for detection. The device can include an alarm unit 216C that outputs an alarm when a preset potassium amount rate is exceeded or not met. When a preset blood serum potassium amount is exceeded, it is also possible to generate a control signal that is received by the central control unit 210 of the blood treatment apparatus via line 217, such that it is possible to engage with the machine control of the blood treatment apparatus.

Figure 13:
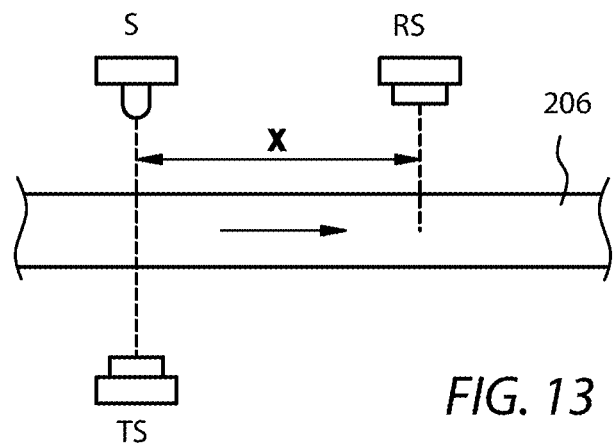
FIG. 13 is a representation of an embodiment of a measurement apparatus for reflection and transmission measurements.

In a specific UV-absorbance embodiment, only reflection and transmission measurements of UV wavelengths, are used. FIG. 13 shows a first alternate embodiment of the measurement apparatus for the reflection and transmission measurements. This embodiment corresponds to the embodiment as shown in FIG. 12, wherein the receivers VS and SS for the forward and lateral scatter have been omitted. Corresponding parts are therefore identified by the same reference signs. The measurement apparatus of FIG. 13 allows both receivers TS and RS to measure reflected and/or transmitted UV radiation simultaneously.

Figure 14:
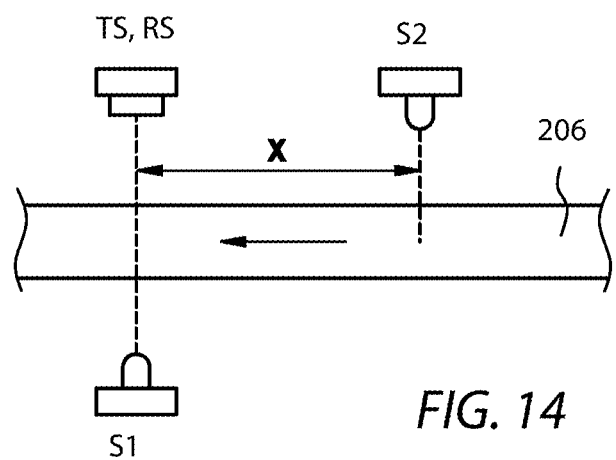
FIG. 14 is a representation of another embodiment of a measurement apparatus for reflection and transmission measurements.

FIG. 14 shows an alternate embodiment that includes a measurement path for the transmission measurement with a transmitter S1 and a receiver TS, RS that is also used for the reflection measurement. A second transmitter S2 is provided for the reflection measurement that is disposed, observing a spacing x of the measurement path, for the transmission measurement. This measurement apparatus does not allow for simultaneous but only for alternate measurements using the two measuring methods. For the transmission measurement, the computing and analyzer unit 16 activates the transmitter S1 for the transmission measurement and deactivates the transmitter S2 for the reflection measurement, while the transmitter S1 is deactivated for the reflection measurement and the transmitter S2 is activated for the reflection measurement. Both measurements can be done immediately in succession.

These exemplary apparatuses according to the present invention allow for a non-invasive, continuous detection of blood serum potassium in whole blood. The apparatuses are characterized by a simple hardware setup and easy analysis of the measured results. The apparatuses can be used in any blood treatment apparatus comprising an extracorporeal blood circuit. For quality assurance purposes, it is also feasible to use the apparatus for detecting blood serum potassium concentrations in units of stored blood. To this end, the receiving unit can be configured for accommodating a unit of stored blood or a hose line on a unit of stored blood.

Figure 15:
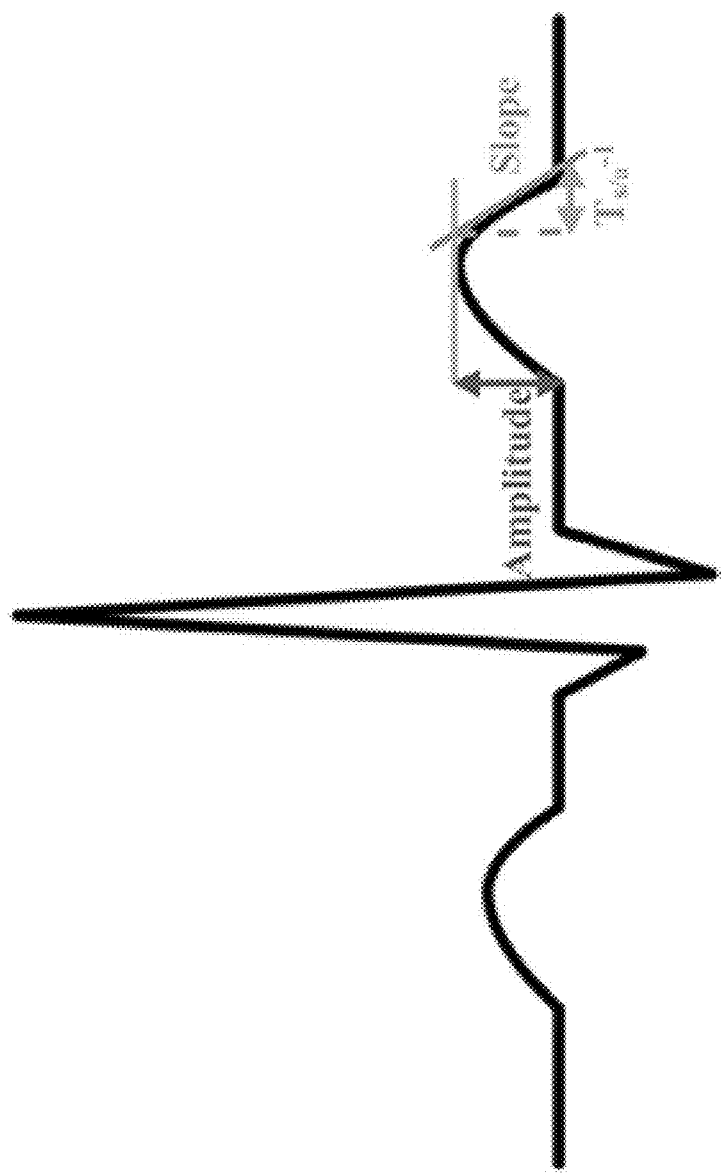
FIG. 15 is a diagram of a typical QRS-T-wave complex from an idealized electrocardiogram together with a schematic explanation of the negative slope and the amplitude of the T wave, which are used to compute the ratio of T wave downslope-to-amplitude (Ts/A) for the purpose of estimating blood serum potassium.

FIG. 15 shows a typical QRS-T-wave complex from an idealized electrocardiogram (ECG) and shows how to define the negative slope and amplitude of the T wave, which can be used to compute the ratio TS/A for estimating extracellular K+ concentration in the patient from whom the ECG was obtained. As can be seen from FIG. 16, the inverse of the TS/A ratio, i.e., (TS/A [s−1]), correlates squarely with the concentration of extracellular K+, as was established in the article of Corsi et al., Noninvasive quantification of blood potassium concentration from ECG in hemodialysis patients, SCIENTIFIC REPORTS, 7:42492, DOI: 10.1038/srep42492 (published Feb. 15, 2017), which is herein incorporated by reference in its entirety. Thus, by taking ECG measurements from a patient, computing a TS/A ratio value or an averaged TS/A ratio value, and comparing the value to a graph, matrix, table, or look-up table, for example, in a computer memory, the concentration of extracellular K+ in the patient can be estimated non-invasively, without the need to calibrate or sterilize a potassium sensor. The method also affords a computation of extracellular K+ concentration in the patient without the need to irradiate the patient's blood or flow the patient's blood through a special flow channel, cartridge, or other analysis chamber. Moreover, the method provides a safe and easy way to analyze the concentration of extracellular K+ in the patient before, during, and after a dialysis treatment. Furthermore, the use of, addition of, and/or infusion of potassium or supplemental potassium, to a dialysate, can be controlled based on the concentration of extracellular K+ so calculated.

The comparative data and/or correlating potassium concentrations can come from data prepared by recording ECGs and comparing the TS/A values to actual blood serum potassium values obtained by blood draws from the respective patients at points in time or periods of time corresponding to when the ECGs were recorded. As an example, 12-lead Holter ECG recordings obtained from an H12+ machine (Mortara Instrument, Inc., Milwaukee, Wis.), can be retrospectively analyzed. The most significant two eigenleads, associated with the first two eigenvalues, can be used to calculate the downslope and the amplitude of the T-wave for each beat. An ECG-based potassium estimator (KECG) can be defined as a quadratic function of the median value of TS/A, automatically computed over a 2-minute window at intervals of 15 minutes. ECG data can be exported and analyzed by implementing a dynamic-link library that interfaces to post-processing software also available from Mortara Instrument, Inc. as the SuperECG/Spectrum.

Historical data from testing done on the same patient can be used to build a database. Population data from testing done on multiple patients can be used to build a database. From time to time, actual blood-draw testing can be used to ensure the ECG-based potassium estimator is providing accurate estimates and to further build a database of estimates. Blood sampling and analysis in an off-line machine such as the OPTIC, CCA-TS2 Analyzer (OPTI Medical Systems, Inc., Roswell, Ga.), can be used to check estimates, be combined with ECG records to build a database, or both.

Figure 16:
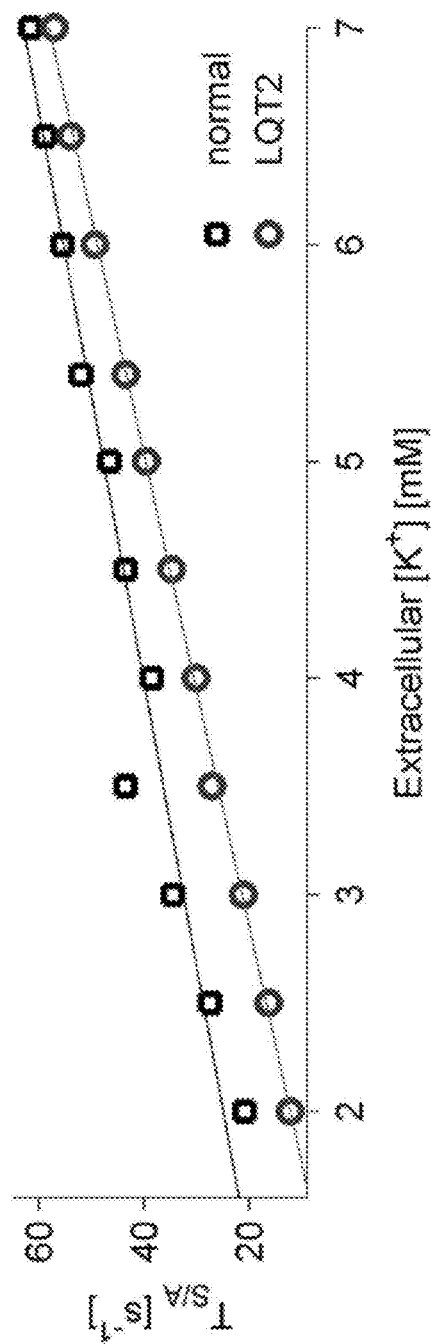
FIG. 16 is a graph showing the relationship between Ts/A and extracellular [$K^+$] (in mM) in a control group (squares) and in a group of congenital long QT type 2 (LQT2) patients (circles).

FIG. 16 shows a database in the form of a graph of extracellular potassium (K+) concentration values measured by standard laboratory analysis, and their correlation with computed TS/A values obtained from concurrently taken ECG records. The graph shows the relationship between TS/A and extracellular potassium ([K+], in mM) in a control group (squares) and in a group of congenital long QT type 2 (LQT2) patients (circles). More details about the relationship and graph are provided in the Corsi et al. article mentioned above, which is incorporated herein in its entirety by reference. Other methods and systems that can be used for non-invasively computing extracellular [K+] values based on ECG data are described in U.S. Pat. No. 9,561,316 B2 to Gerber et al., U.S. Pat. No. 9,456,755 B2 to Soykan et al., and U.S. Patent Application Publication No. US 2017/0000936 A1 to Soykan et al., each of which is incorporated herein in its entirety by reference.

Many methods and devices for in-line monitoring of the potassium during hemodialysis, and that can be used according to the present invention, include those described in Sharma et al., On-line monitoring of electrolytes in hemodialysis: on the road towards individualizing treatment, Expert Review of Medical Devices, 13:10, 933-943, DOI: 10.1080/17434440.2016.1230494 (2016), which is incorporated herein in its entirety by reference.

Ion-selective electrodes can be used to measure or otherwise sense potassium concentrations in blood, dialysate, or both, for example, including blood to be treated, treated blood, fresh dialysate, and used dialysate. ISEs can discriminate between ions. An ideal ISE responds to only one single type of ion in a mixed solution. The ISE can comprise an electrochemical sensor wherein a potentiometric signal is measured as output. A galvanic cell is formed by immersing a pair of electrodes in a solution. The difference in potential of the two electrodes, known as electromotive force (EMF), is then measured. If the potential of one of the electrodes, i.e., a reference electrode, is constant while the other electrode, i.e., an indicator electrode, follows the Nernst equation, then the EMF can be measured. Basically, measured EMF of calibrator fluid(s) and sample are translated into the activity of the ionic species of the sample by means of the Nernst equation. Once calibrated with known concentrations of solution, the EMF can then be related to the analyte concentration of a sample solution, provided the Nernst equation is met. ISEs can be classified based on the type of membrane material as glass, crystalline, or polymeric. ISEs can be used in clinical off-line analysis, or in-line using a flow cell, to measure electrolytes in samples of whole blood, plasma, fresh dialysate, and used dialysate. Potassium concentrations can be measured using multichannel analyzers by indirect ISE potentiometry. Exemplary ISE devices and methods, and flow channels and cassettes that can be used therewith, are described in U.S. Pat. No. 4,995,959 to Metzner and U.S. Pat. No. 6,752,172 B2 to Lauer, each of which is incorporated herein in its entirety by reference. An ISE can use a passive polymeric membrane comprising ionophores, which determines the ion-selectivity and thus forms a significant part of the electrode. ISEs can be integrated in the in-line monitoring of electrolytes during dialysis. The standard electrode potential of an ISE changes over time, thus it can be frequently recalibrated.

Devices and methods based on optical measurements can be used to measure or otherwise sense potassium concentrations in blood, dialysate, or both, for example, including blood to be treated, treated blood, fresh dialysate, and used dialysate. Optical sensors offer potential benefits including an inherent immunity to electromagnetic interference, intrinsically contactless through-window interaction, and no damage to the host system. This offers improved biocompatibility and less vulnerability to fouling, the absence of electrical currents, and the potential of simultaneous measurements of multiple substances. The basic components that can be used for optical measurement are a light/illuminating/irradiating source, the fluid (stream) to be measured, an optical spectral sorting element a detector for optical readout, and a signal processor. The light/illumination or irradiating source can be a light-emitting diode (LED), an organic LED, a laser, a quantum dot, an incandescent source, a fluorescent source, or the like. The optical spectral sorting element can be a filter, a set of filters, a diffraction grating, a prism, or the like. The detector for optical readout can be a photodiode, a photomultiplier tube, a charge-coupled device, or the like. The signal processor can comprise a computer, a CPU, a microprocessor, or the like. Optical sensors, namely, ultraviolet (UV) absorbance and near-infrared (NIR) spectroscopy systems and methods can be used to estimate potassium concentrations in fresh and spent dialysate and can be used to improve the dialysate dosing and prescriptions. A UV absorbance method can utilize a UV-light source (190-400 nm), a UV-transparent sample holder (cuvette), and a photodetector. As an example, UV-transmittance can be used for continuously monitoring the removal of potassium. Dialysate can be monitored during HD using UV-absorbance, for example, for monitoring the amount of potassium in spent dialysate. Measurements on collected dialysate samples can be compared with on-line measurements. A spectrophotometer can be connected to the fluid outlet of the dialysis machine and the spent dialysate can be made to pass through a cuvette. UV-absorbance can be used to calculate the dialysis dose.

NIR (750-2500 nm) spectrometry can be used for on-line monitoring of potassium during dialysis. A temperature-controlled acousto-optical filter-based spectrometer can be used to measure potassium concentration in used or spent dialysate, blood, or treated blood. NIR spectroscopy uses interference and diffraction.

Flame photometry can be used to measure or otherwise sense potassium concentrations in blood, dialysate, or both, for example, including blood to be treated, treated blood, fresh dialysate, and used dialysate. Flame photometry is an atomic emission spectroscopy technique used to determine the concentration of certain metal ions. The solution is nebulized and injected into a nonluminous gas flame resulting in emission of a characteristic flame coloring. The spectral emission 'fingerprint' of the flame identifies the element while the intensity indicates the concentration of the elements. This technique is well established and widely used in clinical laboratories for electrolyte concentration measurement.

Figure 17A:
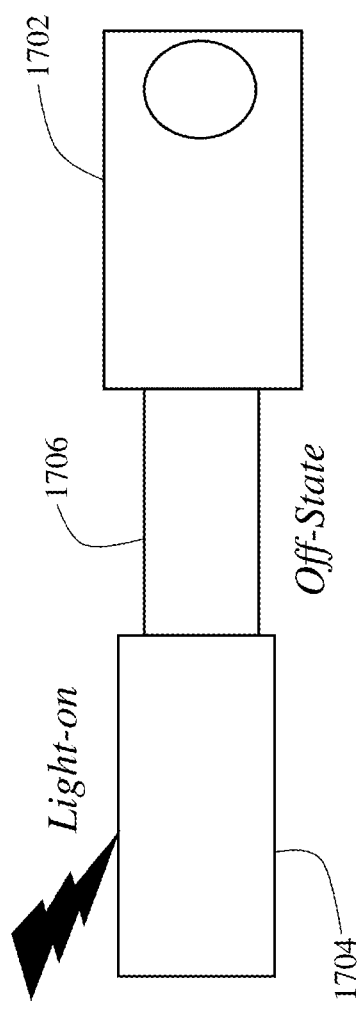
FIGS. 17A and 17B are schematic illustrations of a fluorescent PET sensor molecule wherein a fluorophore part is responsible for fluorescence emission and the receptor is designed for a potassium cation (K), shown in absence of a targeted analyte such that fluorescence is absent (FIG. 17A: OFF-state), and shown with an analyte (indicated by "A") captured by the receptor such that the molecule is excited and emits fluorescence (FIG. 17B: ON-state).
Figure 17B:
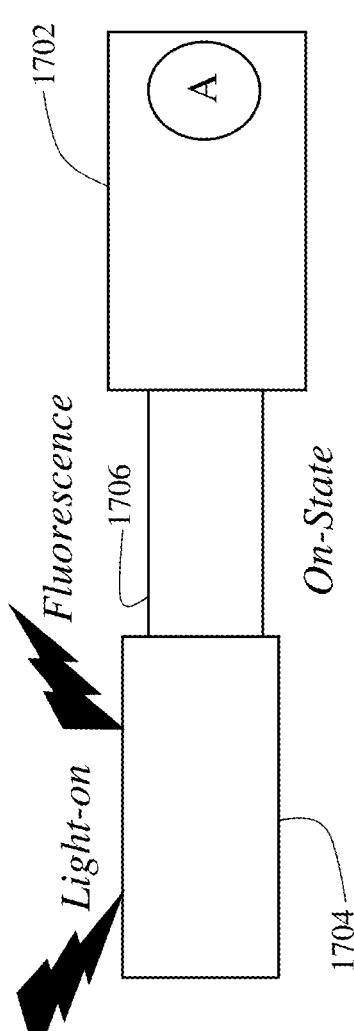

Fluorescent photo-induced electron transfer sensors can be used to measure or otherwise sense potassium concentrations in blood, dialysate, or both, for example, including blood to be treated, treated blood, fresh dialysate, and used dialysate. The sensor molecules for potassium (K+), based on a fluorescent photo-induced electron transfer (PET) process, can be designed based on a 'fluorophore-spacer-receptor' format as depicted in FIGS. 17A and 17B. A receptor 1702 is schematically shown in FIG. 17A, absent an analyte. Receptor 1702 is spaced from a fluorophore 1704 by a spacer 1706. Due to the absence of an analyte, for example, a cationic species, an electron gets transferred from receptor 1702 to fluorophore 1704 which results in quenching the fluorescence process. This is called an "Off-State" of the sensor. If, instead, an analyte (A) is present, as is schematically shown in FIG. 17B, then there will be an emission of a fluorescence signal from fluorophore 1704. This is called an "On-State" of the sensor. Fluorescence intensity gives the specific analyte concentration. The choice of fluorophore can be entirely based on excitation and emission wavelengths, whereas the receptor can be chosen based on the analyte to be determined. Therefore, cheap and stable visible spectrum (400-700 nm) light sources like LEDs or small lasers can be used for excitation. PET sensors can be used to analyze samples of whole blood in a static medium. The PET molecules can be fixed on a substrate that acts like a cassette. After injecting the sample into this cassette, it is inserted into an optical readout device. An electrolyte analyzer can utilize an LED source as an excitation source, and photodiodes can be used to collect the fluorescence emission. The PET sensor molecule can be coated on a micro-structured optical fiber tip. A portion of a patient's whole blood can be diverted from an extracorporeal blood circuit to a port, flow cell, or testing cell where a PET sensor can be used to determine the concentration of potassium in the whole blood.

Laser-induced breakdown spectroscopy can be used to measure or otherwise sense potassium concentrations in blood, dialysate, or both, for example, including blood to be treated, treated blood, fresh dialysate, and used dialysate. The elemental analysis in LIBS is very similar to flame photometry, but instead of a gas flame, it uses a strongly focused laser pulse to produce a minuscule (typically 2-3-μm diameter) plasma discharge (the 'breakdown') directly in the fluid stream. No nebulizer is needed. Due to the high plasma temperature, neighboring atoms are excited, and, when falling back to their ground state, send out light with a characteristic spectral line pattern. Just as in flame photometry, the elemental composition can then be determined by resolving the spectrum of the resulting emission spectrum. The atom-specific spectral peak amplitudes indicate specific ion concentration. LIES thus is a truly 'through-the-window' measurement technology that does not require any direct contact with the fluid. The absence of an ion-selective membrane circumvents drift problems from membrane fouling issues or other Nernst equation disturbances.

Figure 18:
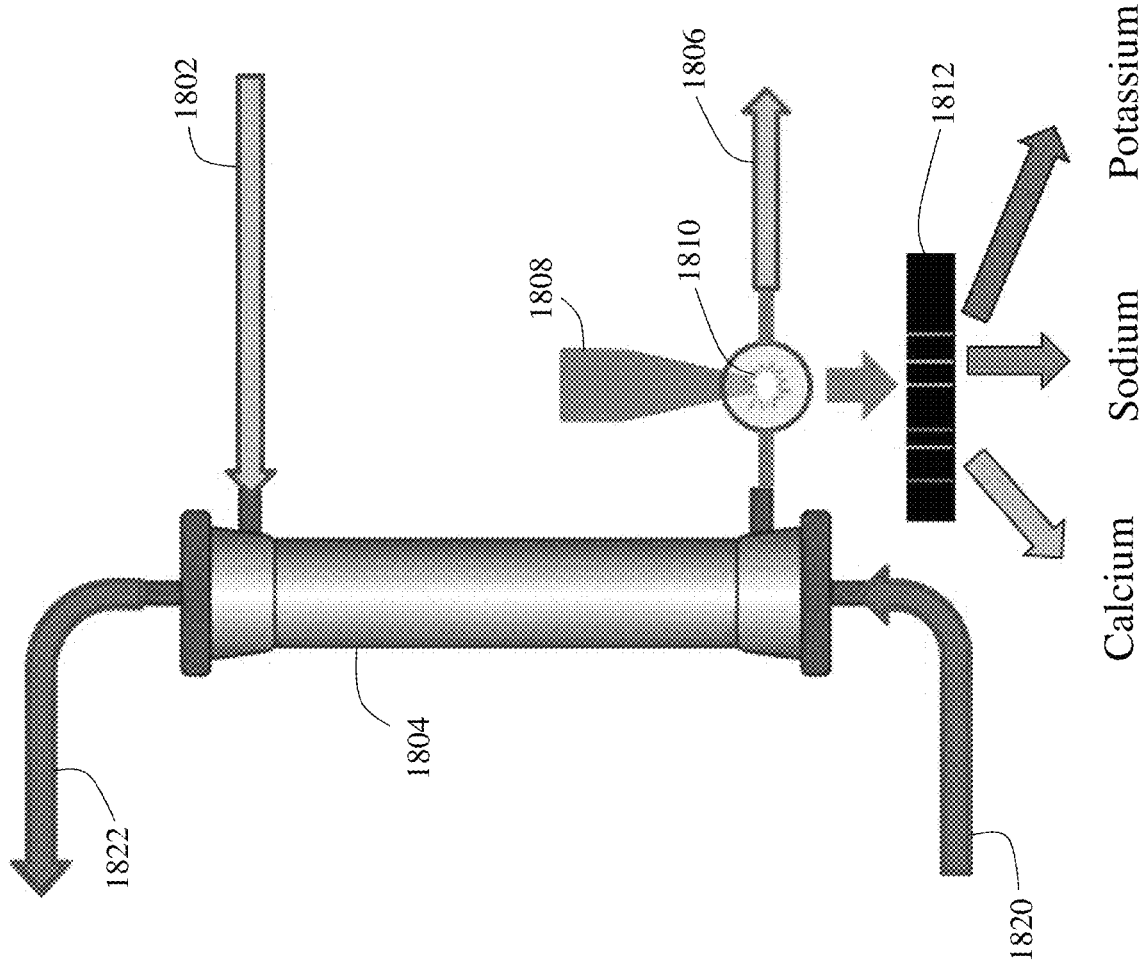
FIG. 18 is a schematic diagram showing the principle of laser-induced breakdown spectroscopy (LIES), whereby a tiny volume inside a dialysate stream is temporarily atomized by a focused high-energy pulsed laser, light emitted from this high-temperature spark is collected and dispersed, and the atoms present in the specimen can be identified by specific peaks in the atomic emission spectrum.

In FIG. 18, the principle of laser-induced breakdown spectroscopy (LIES) is shown. Fresh dialysate flows through a fresh dialysate conduit 1802, and through a dialysate side (not shown) of a dialyzer 1804 wherein ion exchange with blood occurs, to form used dialysate. The blood is supplied from an extracorporeal blood circuit that includes an arterial, from-patient, blood conduit 1820, the blood side (not shown) of dialyzer 1804, and a venous, to-patient, return conduit 1822. The used dialysate exits dialyzer 1804 and travels through a used dialysate conduit 1806 that includes a sensor window through which a focused high-energy laser pulse is directed from a laser source 1808. A tiny volume inside the used dialysate stream is temporarily atomized by the focused high-energy pulsed laser. Light emitted from the resulting high-temperature spark 1810 is collected and dispersed, and the atoms present in the specimen can be identified by specific peaks in the atomic emission spectrum 1812. The advantages of LIBS include real-time analysis of elements, no sample preparation, and high sensitivity, for example, down to a ppm level if a high enough laser power is used. The application of LIBS technology can be used for the on-line determination of potassium and other electrolytes within flowing dialysate.

Microsystem technologies can be used to measure or otherwise sense potassium concentrations in blood, dialysate, or both, for example, including blood to be treated, treated blood, fresh dialysate, and used dialysate. Microsystem technologies can be used for electrolyte monitoring. High-precision devices can be manufactured in a very cost-effective way. Soft lithography using polymeric materials for lab-on-a-chip microfluidic devices provide a platform for point-of-care (POC)-based devices. There are inherent advantages of microsystem technologies, namely, (1) smaller sizes ranging from micrometers to nanometers, (2) fast response time due to the small samples sizes, (3) high precision, (4) cost-effectiveness, and (5) ease of integration. The detection system can be based either on electrochemical (conductivity, potentiometric), electrical (impedance), or optical (absorbance, reflectance, fluorescence).

One of the most sensitive sensing techniques is based on molecular fluorescence with advantages in terms of specificity, sensitivity, and detection. Microfluidic systems based on electro-osmotic flow or electrophoretic separation can be used that employ ion concentration measurement using conductivity detection. This detection scheme is capable of simultaneously analyzing multiple ions in both contact and contactless modes. A portable critical care analyzer system called i-STAT, based on ion-selective potentiometric sensing, can be used. The system consists of a hand-held analyzer and a disposable cartridge. The cartridge contains a series of ion-sensitive electrodes over which the analysis fluid passes. Such a system can be used as a POC system to analyze whole blood. The i-STAT system can be used in an HD unit to analyze potassium. The i-STAT system can also be used to analyze potassium in dialysate fluid.

Microfluidic systems and devices comprising polydimethylsiloxane (PDMS)-fabricated micropumps and microchannels can be used with ISEs patterned on a glass substrate to analyze potassium. Such devices exhibit good sensitivity and reproducibility. The optical sensing schemes in microfluidic devices can be classified as 'off-chip' and 'on-chip,' respectively. The off-chip approach can use the exterior coupling of optical components into the device, whereas the on-chip approach can apply optical functionalities that are integrated into the device. The optical components used in such sensing systems can comprise LEDs or lasers as a light source, optical fibers or integrated waveguides for light guiding, lenses and filters for spectral separation, and a photodiode or charged-coupled device for detection. The basic optical components of such a system are shown in FIG. 19.

Figure 19:
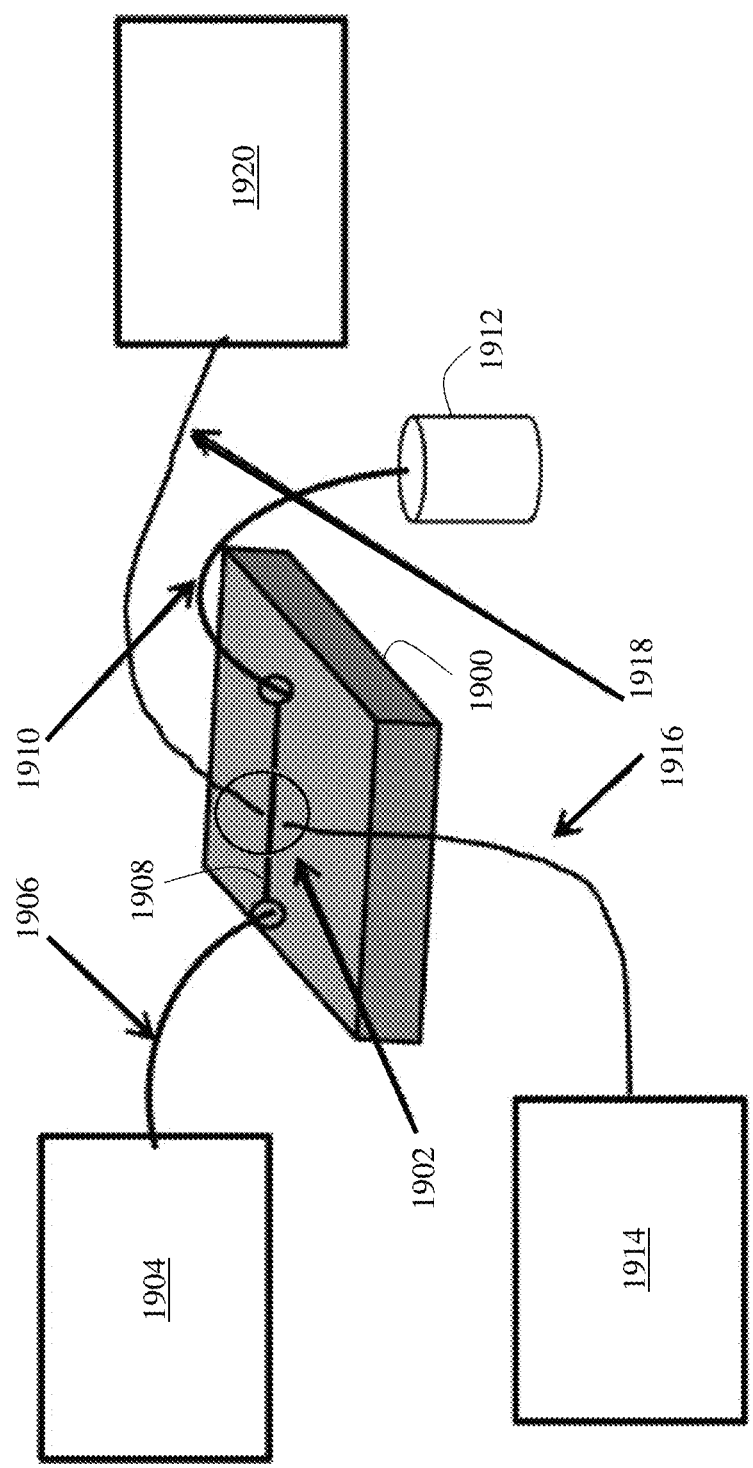
FIG. 19 is a schematic diagram of a microfluidic optical sensor setup that can be used according to the present invention.

FIG. 19 shows a microfluidic chip 1900, that includes an interrogation zone 1902. A syringe pump 1904 pumps a sample, for example, of blood or used dialysate, through a fluid inlet 1906, and into and through a microfluidic channel 1908 that passes through interrogation zone 1902. The end of microfluidic channel 1908 is in fluid communication with a fluid outlet 1910 in the form of a conduit through which the interrogated sample can pass to a waste canister 1912.

A light source 1914 generates excitation radiation of one or more wavelengths selected to excite fluorophores in the sample. The excitation radiation is directed to interrogation zone 1902 through an optical fiber 1916. Fluorescence emissions resulting from excitation of the fluorophores is gathered or collected by an optical fiber 1918, and appropriate optics if needed, and transmitted through optical fiber 1918 to a fluorescence detector 1920 where the fluorescence can be spectroscopically separated, quantitated, and analyzed.

Optical sensing can be implemented either by measuring the direct change in light intensity or one or more other optical properties, for example, absorbance, fluorescence, chemiluminescence, a change in the wavelength, a phase change, or polarization of light. Spectroscopic detection can be used. The advantages include high sensitivity and low background noise. In order to couple the external macroscopic elements into microscopic detection areas, fiber-coupling grooves can be fabricated in a single-step fabrication process for the integration of optical fibers. Optical fibers and a fabricated ball lens can be used for light coupling in taking absorbance measurements. Sensors can be reused and regenerated after rinsing with HCl solution. A device can be fabricated in a PDMS and glass substrate for fluorometric determination of potassium ions (K+) based on a fluorescent molecular sensor calix-bodipy. The device can comprise a Y-shaped microchannel molded in PDMS and fixed on a glass substrate, and optical fibers can be used for excitation and fluorescence light collection. Flow injection analysis of aqueous solutions of potassium ions can be carried out with a detection limit of 0.5 mM.

MEMS technologies can be used and have enabled the integration of mechanical and electrical components along with a fluidic part. Many MEMS-fabricated passive optical components like mirrors, lenses, and filters can be used and can provide miniaturized light sources and optical detectors. The integration of waveguides and lenses can improve the optical path length for absorbance measurement or light focusing for fluorescence measurement. A capillary-assembled microchip can be used for sensing potassium. A multifunctional microchip can be used that comprises a microchannel network fabricated in PDMS embedded with chemically functionalized square capillaries. The network and outer diameter of capillaries can have the same diameter. The ion sensing square capillaries can be prepared by attaching ion-selective optode membranes to the inner walls of the capillaries. The device can analyze potassium with a working range of from 10-5 to 10-1 M.

The present invention includes the following aspects/embodiments/features in any order and/or in any combination:

1. A dialysis method comprising:
   performing a dialysis treatment on a patient, the patient having blood including blood serum;
   sensing a concentration of potassium in the patient's blood serum, the sensing comprising generating a sensed value of blood serum potassium concentration;
   receiving with a control and computing unit the sensed value;
   comparing the sensed value with one or more values stored in a memory;
   generating a control signal based on the comparison; and
   modifying the dialysis treatment by infusing potassium solution into treatment dialysate that is used during the dialysis treatment, based on the control signal.
2. The dialysis method of any preceding or following embodiment/feature/aspect, further comprising storing the sensed value of blood serum potassium concentration in the memory.
3. The dialysis method of any preceding or following embodiment/feature/aspect, wherein the memory has stored therein patient-historical data pertaining to sensed blood serum potassium concentration values of the patient, obtained under different patient parameters.
4. The dialysis method of any preceding or following embodiment/feature/aspect, wherein the different patient parameters include at least one parameter based on the length of time since a last dialysis treatment was carried out on the patient.
5. The dialysis method of any preceding or following embodiment/feature/aspect, further comprising inputting patient information including a time-since-last-treatment value, wherein the control and computing unit generates the control signal based also on the inputted patient information.
6. The dialysis method of any preceding or following embodiment/feature/aspect, further comprising comparing the sensed value of blood serum potassium concentration to blood serum potassium concentration values of a population of different patients obtained under different patient parameters.
7. The dialysis method of any preceding or following embodiment/feature/aspect, further comprising:
   generating the control signal based on the sensed value of blood serum potassium concentration and based on population data stored in the memory; and
   supplying a concentrated solution of a potassium salt at a first rate and for a first period of time, into a dialysate circuit used for the dialysis treatment, based on the control signal.
8. The dialysis method of any preceding or following embodiment/feature/aspect, further comprising regenerating dialysate used in the treatment, with a sorbent cartridge.
9. The dialysis method of any preceding or following embodiment/feature/aspect, wherein the sensing the concentration of potassium comprises using an ion selective electrode pair to generate ion selective electrode measurements, and the method further comprises calculating the concentration of potassium in the patient's blood serum based on the ion selective electrode measurements.
10. The dialysis method of any preceding or following embodiment/feature/aspect, wherein the sensing the concentration of potassium comprises sensing transmission of ultraviolet light directed through the patient's blood.
11. The dialysis method of any preceding or following embodiment/feature/aspect, wherein the sensing the concentration of potassium comprises sensing transmission of near-infrared radiation directed through the patient's blood.
12. The dialysis method of any preceding or following embodiment/feature/aspect, wherein the sensing the concentration of potassium comprises sensing flame photometry emissions resulting from subjecting a portion of the patient's blood to flame photometry.
13. The dialysis method of any preceding or following embodiment/feature/aspect, wherein the sensing the concentration of potassium comprises sensing fluorescent photo-induced electron transfer resulting from subjecting a portion of the patient's blood to fluorescent excitation radiation.
14. The dialysis method of any preceding or following embodiment/feature/aspect, wherein the sensing the concentration of potassium comprises sensing spectroscopic emissions resulting from subjecting a portion of the patient's blood to laser-induced breakdown spectroscopy.
15. The dialysis method of any preceding or following embodiment/feature/aspect, wherein the sensing the concentration of potassium comprises:
   flowing a portion of the patient's blood in a microfluidic channel on a microfluidic chip;
   directing electromagnetic radiation through an optical fiber and toward the portion of the patient's blood in the microfluidic channel, to cause fluorescent emissions from the microfluidic channel;

directing the fluorescent emissions through a second optical fiber and toward a fluorescence detector; and detecting the fluorescent emissions with the fluorescence detector.

16. The dialysis method of any preceding or following embodiment/feature/aspect, wherein the sensing the concentration of potassium comprises:

sensing electrocardiogram signals corresponding to a heartbeat of the patient, from an electrocardiogram lead connected to the patient;

determining the amplitude of a T wave component of a first heartbeat signal of the electrocardiogram signals;

determining a negative slope of the T wave component;

computing a ratio of the negative slope to the amplitude; and correlating the ratio to a predetermined blood serum potassium concentration value stored in the memory.

17. A dialysis method comprising:

performing a dialysis treatment on a patient, the patient having blood including blood serum;

sensing a concentration of potassium in used dialysate formed by the dialysis treatment, the sensing comprising generating a sensed value of potassium concentration in the used dialysate;

receiving, with a control and computing unit, the sensed value;

comparing the sensed value with one or more values stored in a memory;

generating a control signal based on the comparison; and modifying the dialysis treatment by infusing potassium solution into fresh treatment dialysate that is used during the dialysis treatment, based on the control signal.

18. The dialysis method of any preceding or following embodiment/feature/aspect, further comprising storing the sensed value in the memory.

19. The dialysis method of any preceding or following embodiment/feature/aspect, wherein the memory has stored therein patient-historical data pertaining to sensed values of potassium concentrations in used dialysate resulting from previous dialysis treatments on the patient, obtained under different patient parameters.

20. The dialysis method of any preceding or following embodiment/feature/aspect, wherein the different patient parameters include at least one parameter based on the length of time since a last dialysis treatment was carried out on the patient.

21. The dialysis method of any preceding or following embodiment/feature/aspect, further comprising inputting patient information including a time-since-last-treatment value, wherein the control and computing unit generates the control signal based also on the inputted patient information.

22. The dialysis method of any preceding or following embodiment/feature/aspect, further comprising comparing the sensed value of potassium concentration in the used dialysate to potassium concentration values in used dialysate resulting from dialysis treatments previously conducted on a population of different patients obtained under different patient parameters.

23. The dialysis method of any preceding or following embodiment/feature/aspect, further comprising:

generating a control signal based on the sensed value of potassium concentration in the used dialysate and based on population data stored in the memory; and supplying a concentrated solution of a potassium salt at a first rate and for a first period of time, into a dialysate circuit used for the dialysis treatment.

24. The dialysis method of any preceding or following embodiment/feature/aspect, further comprising regenerating dialysate used in the treatment, with a sorbent cartridge.

25. The dialysis method of any preceding or following embodiment/feature/aspect, further comprising computing, with the control and computing unit, a blood serum potassium concentration value based on the sensed value of potassium concentration in the used dialysate.

26. The dialysis method of any preceding or following embodiment/feature/aspect, wherein the sensing the concentration of potassium comprises using an ion selective electrode pair to generate ion selective electrode measurements, and the method further comprises calculating the concentration of potassium in the used dialysate formed by the dialysis treatment, based on the ion selective electrode measurements.

27. The dialysis method of any preceding or following embodiment/feature/aspect, wherein the sensing the concentration of potassium comprises using an ion selective electrode pair to generate ion selective electrode measurements, and the method further comprises calculating the concentration of potassium in the patient's blood serum, based on the ion selective electrode measurements.

28. The dialysis method of any preceding or following embodiment/feature/aspect, wherein the sensing the concentration of potassium comprises sensing transmission of ultraviolet light directed through the used dialysate.

29. The dialysis method of any preceding or following embodiment/feature/aspect, wherein the sensing the concentration of potassium comprises sensing transmission of near-infrared radiation directed through the used dialysate.

30. The dialysis method of any preceding or following embodiment/feature/aspect, wherein the sensing the concentration of potassium comprises sensing flame photometry emissions resulting from subjecting a portion of the used dialysate to flame photometry.

31. The dialysis method of any preceding or following embodiment/feature/aspect, wherein the sensing the concentration of potassium comprises sensing fluorescent photo-induced electron transfer resulting from subjecting a portion of the used dialysate to fluorescent excitation radiation.

32. The dialysis method of any preceding or following embodiment/feature/aspect, wherein the sensing the concentration of potassium comprises sensing spectroscopic emissions resulting from subjecting a portion of the used dialysate to laser-induced breakdown spectroscopy.

33. The dialysis method of any preceding or following embodiment/feature/aspect, wherein the sensing the concentration of potassium comprises:

flowing a portion of the used dialysate in a microfluidic channel on a microfluidic chip;

directing electromagnetic radiation through an optical fiber and toward the portion of the used dialysate in the microfluidic channel, to cause fluorescent emissions from the microfluidic channel;

directing the fluorescent emissions through a second optical fiber and toward a fluorescence detector; and detecting the fluorescent emissions with the fluorescence detector.

34. The dialysis method of any preceding or following embodiment/feature/aspect, wherein the patient has a peritoneum, the dialysis treatment comprises a peritoneal dialysis treatment, and the used dialysate comprises a used peritoneal dialysis solution that has dwelled in the patient's peritoneum.

The present invention can include any combination of these various features or embodiments above and/or below as set forth in sentences and/or paragraphs. Any combination of disclosed features herein is considered part of the present invention and no limitation is intended with respect to combinable features.

Applicants specifically incorporate the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

What is claimed is:

1. A dialysis method comprising:
   receiving patient parameters including a time-since-last-treatment value, by a control and computing unit that comprises a processor and a memory;
   performing a dialysis treatment on a patient, the patient having blood including blood serum and the dialysis treatment comprising dialyzing the patient's blood with a treatment dialysate;
   sensing a concentration of potassium in the patient's blood serum, the sensing comprising generating a sensed value of blood serum potassium concentration;
   receiving with the control and computing unit the sensed value;
   comparing, using the processor, the sensed value with one or more patient-historical data values stored in the memory, the patient-historical data pertaining to sensed blood serum potassium concentration values resulting from dialysis treatments performed on the patient under different patient parameters comprising at least one parameter based on a length of time since a last dialysis treatment was carried out on the patient;
   generating, using the processor, a control signal based on the comparison and the received patient parameters;
   sending the control signal to a potassium infusion circuit that is configured to receive the control signal; and
   modifying the dialysis treatment by infusing potassium solution into treatment dialysate that is then used during the dialysis treatment, the infusion being based on the control signal received by the potassium infusion circuit.

2. The dialysis method of claim 1, further comprising storing the sensed value of blood serum potassium concentration in the memory.

3. The dialysis method of claim 1, further comprising:
   comparing the sensed value of blood serum potassium concentration to blood serum potassium concentration values of a population of different patients obtained under different patient parameters;
   generating the control signal based on the sensed value of blood serum potassium concentration and based on population data stored in the memory; and
   supplying a concentrated solution of a potassium salt at a first rate and for a first period of time, into a dialysate circuit used for the dialysis treatment, based on the control signal.

4. The dialysis method of claim 1, wherein the sensing the concentration of potassium comprises using an ion selective electrode pair to generate ion selective electrode measurements, and the method further comprises calculating the concentration of potassium in the patient's blood serum based on the ion selective electrode measurements.

5. The dialysis method of claim 1, wherein the sensing the concentration of potassium comprises sensing fluorescent photo-induced electron transfer resulting from subjecting a portion of the patient's blood to fluorescent excitation radiation.

6. The dialysis method of claim 1, wherein the sensing the concentration of potassium comprises:
   flowing a portion of the patient's blood in a microfluidic channel on a microfluidic chip;
   directing electromagnetic radiation through an optical fiber and toward the portion of the patient's blood in the microfluidic channel, to cause fluorescent emissions from the microfluidic channel;
   directing the fluorescent emissions through a second optical fiber and toward a fluorescence detector; and
   detecting the fluorescent emissions with the fluorescence detector.

7. The dialysis method of claim 1, wherein the sensing the concentration of potassium comprises:
   sensing electrocardiogram signals corresponding to a heartbeat of the patient, from an electrocardiogram lead connected to the patient;
   determining the amplitude of a T wave component of a first heartbeat signal of the electrocardiogram signals;
   determining a negative slope of the T wave component;
   computing a ratio of the negative slope to the amplitude; and
   correlating the ratio to a predetermined blood serum potassium concentration value stored in the memory.

8. A dialysis method comprising:
   receiving patient parameters including a time-since-last-treatment value, by a control and computing unit that comprises a processor and a memory;
   performing a dialysis treatment on a patient, the patient having blood including blood serum and the dialysis treatment comprising dialyzing the patient's blood with a treatment dialysate to form used dialysate;
   sensing a concentration of potassium in the used dialysate formed by the dialysis treatment, the sensing comprising generating a sensed value of potassium concentration in the used dialysate;
   receiving, with the control and computing unit, the sensed value;
   comparing, using the processor, the sensed value with one or more patient-historical data values stored in the memory, the patient-historical data pertaining to sensed used dialysate potassium concentration values resulting from dialysis treatments performed on the patient under different patient parameters comprising at least one parameter based on a length of time since a last dialysis treatment was carried out on the patient;

generating, using the processor, a control signal based on the comparison and the received patient parameters;

sending the control signal to a potassium infusion circuit that is configured to receive the control signal; and modifying the dialysis treatment by infusing potassium solution into fresh treatment dialysate that is then used during the dialysis treatment, the infusing being based on the control signal received by the potassium infusion circuit.

9. The dialysis method of claim 8, further comprising comparing, using the processor, the sensed value of potassium concentration in the used dialysate to potassium concentration values that are stored in the memory, for used dialysate resulting from dialysis treatments previously conducted on a population of different patients obtained under different patient parameters, wherein the generating the control signal, using the processor, is also based on the comparison of the sensed value of potassium concentration in the used dialysate to the potassium concentration values that are stored in the memory, for used dialysate resulting from the dialysis treatments previously conducted on the population of different patients obtained under different patient parameters.

10. The dialysis method of claim 9, further comprising:

supplying a concentrated solution of a potassium salt at a first rate and for a first period of time, into a dialysate circuit used for the dialysis treatment.

11. The dialysis method of claim 8, further comprising computing, with the control and computing unit, a blood serum potassium concentration value based on the sensed value of potassium concentration in the used dialysate.

12. The dialysis method of claim 8, wherein the sensing the concentration of potassium comprises using an ion selective electrode pair to generate ion selective electrode measurements, and the method further comprises calculating the concentration of potassium in the used dialysate formed by the dialysis treatment, based on the ion selective electrode measurements.

13. The dialysis method of claim 8, wherein the sensing the concentration of potassium comprises using an ion selective electrode pair to generate ion selective electrode measurements, and the method further comprises calculating the concentration of potassium in the patient's blood serum, based on the ion selective electrode measurements.

14. The dialysis method of claim 8, wherein the sensing the concentration of potassium comprises sensing transmission of ultraviolet light directed through the used dialysate.

15. The dialysis method of claim 8, wherein the sensing the concentration of potassium comprises sensing transmission of near-infrared radiation directed through the used dialysate.

16. The dialysis method of claim 8, wherein the sensing the concentration of potassium comprises:

flowing a portion of the used dialysate in a microfluidic channel on a microfluidic chip;

directing electromagnetic radiation through an optical fiber and toward the portion of the used dialysate in the microfluidic channel, to cause fluorescent emissions from the microfluidic channel;

directing the fluorescent emissions through a second optical fiber and toward a fluorescence detector; and detecting the fluorescent emissions with the fluorescence detector.

17. The dialysis method of claim 8, wherein the patient has a peritoneum, the dialysis treatment comprises a peritoneal dialysis treatment, and the used dialysate comprises a used peritoneal dialysis solution that has dwelled in the patient's peritoneum.

18. The dialysis method of claim 8, further comprising inputting the patient parameters including a time-since-last-treatment value, into the control and computing unit.

* * * * *